(12) United States Patent
Shaver et al.

(10) Patent No.: US 10,899,696 B2
(45) Date of Patent: *Jan. 26, 2021

(54) PROCESSES FOR PURIFYING ACETIC ACID AND HYDRATING ANHYDRIDE

(71) Applicant: CELANESE INTERNATIONAL CORPORATION, Irving, TX (US)

(72) Inventors: Ronald D. Shaver, Houston, TX (US); Yaw-Hwa Liu, Missouri City, TX (US); Mark O. Scates, Houston, TX (US)

(73) Assignee: CELANESE INTERNATIONAL CORPORATION, Irving, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/856,748

(22) Filed: Apr. 23, 2020

(65) Prior Publication Data

US 2020/0247743 A1 Aug. 6, 2020

Related U.S. Application Data

(63) Continuation of application No. 16/165,575, filed on Oct. 19, 2018, which is a continuation of application
(Continued)

(51) Int. Cl.
*C07C 51/44* (2006.01)
*C07C 51/087* (2006.01)
(Continued)

(52) U.S. Cl.
CPC ............ *C07C 51/44* (2013.01); *C07C 51/087* (2013.01); *C07C 51/12* (2013.01); *C07C 51/47* (2013.01); *C07C 51/487* (2013.01); *C07C 51/56* (2013.01)

(58) Field of Classification Search
CPC ....... C07C 51/44; C07C 51/087; C07C 51/12; C07C 51/47; C07C 51/487; C07C 51/56
(Continued)

(56) References Cited

U.S. PATENT DOCUMENTS 2,770,585 A 11/1956 Smith et al.
3,560,560 A 2/1971 Kiff et al.
(Continued)

FOREIGN PATENT DOCUMENTS

CN 1244533 A 2/2000
CN 102442907 A 5/2012
(Continued)

OTHER PUBLICATIONS

Celanese Chemicals, Product Description, "Acetic Acid, Glacial (Ethanoic Acid, Methanecarboxylic Acid)", Acetic Acid, Chemical Abstracts Registry, No. 67-19-7, 2000.
(Continued)

*Primary Examiner* — Deborah D Carr
(74) *Attorney, Agent, or Firm* — Kilpatrick Townsend & Stockton, LLP

(57) ABSTRACT

Processes for purifying acetic acid by distilling a process stream in a column in which acetic anhydride is formed in the lower portion of the column. The product stream withdrawn from the column comprises acetic acid, water at a concentration of no more than 0.2 wt. %, and acetic anhydride at a concentration of no more than 600 wppm. The process further comprises hydrating the acetic anhydride in the product stream to form a purified acetic acid product comprising acetic anhydride at a concentration of no more than 50 wppm.

20 Claims, 2 Drawing Sheets

Related U.S. Application Data

No. 15/863,484, filed on Jan. 5, 2018, now Pat. No. 10,160,714, which is a continuation of application No. 15/348,466, filed on Nov. 10, 2016, now Pat. No. 9,908,835.

(60) Provisional application No. 62/255,060, filed on Nov. 13, 2015.

(51) Int. Cl.
    *C07C 51/56* (2006.01)
    *C07C 51/47* (2006.01)
    *C07C 51/487* (2006.01)
    *C07C 51/12* (2006.01)

(58) Field of Classification Search
    USPC .......................................................... 562/519
    See application file for complete search history.

(56) References Cited

U.S. PATENT DOCUMENTS

| | | | |
|---|---|---|---|
| 3,769,329 A | 10/1973 | Paulik et al. | |
| 4,046,807 A | 9/1977 | Kuckertz | |
| 4,110,372 A | 8/1978 | Hey et al. | |
| 4,115,444 A | 9/1978 | Rizkalla | |
| 4,374,070 A | 2/1983 | Larkins et al. | |
| 5,001,259 A | 3/1991 | Smith et al. | |
| 5,026,908 A | 6/1991 | Smith et al. | |
| 5,144,068 A | 9/1992 | Smith et al. | |
| 5,220,058 A | 6/1993 | Fish et al. | |
| 5,227,524 A | 7/1993 | Jones | |
| 5,292,948 A | 3/1994 | Zoeller et al. | |
| 5,344,976 A | 9/1994 | Jones et al. | |
| 5,625,095 A | 4/1997 | Miura et al. | |
| 5,648,531 A | 7/1997 | Morimoto et al. | |
| 5,731,252 A | 3/1998 | Warner et al. | |
| 5,801,279 A | 9/1998 | Miura et al. | |
| 6,066,762 A | 5/2000 | Yoneda et al. | |
| 6,657,078 B2 | 12/2003 | Scates et al. | |
| 7,678,940 B2 | 3/2010 | Miura et al. | |
| 8,017,802 B2 | 9/2011 | Scates et al. | |
| 8,168,822 B2 | 5/2012 | Scates | |
| 8,759,576 B2 | 6/2014 | Warner et al. | |
| 8,940,932 B2 | 1/2015 | Shimizu | |
| 8,957,248 B2 | 2/2015 | Miura et al. | |
| 9,006,483 B2 | 4/2015 | Shimizu et al. | |
| 9,073,843 B2 | 7/2015 | Shimizu et al. | |
| 9,115,071 B2 | 8/2015 | Shimizu et al. | |
| 9,776,941 B2 | 10/2017 | Shimizu et al. | |
| 9,908,835 B2 * | 3/2018 | Shaver | C07C 51/12 |
| 2006/0011462 A1 | 1/2006 | Horiguchi et al. | |
| 2007/0093676 A1 | 4/2007 | Kojima et al. | |
| 2011/0166386 A1 | 7/2011 | Telgenhoff | |
| 2011/0251422 A1 | 10/2011 | Salisbury | |
| 2012/0123160 A1 | 5/2012 | Barron et al. | |
| 2012/0123610 A1 | 5/2012 | Tupa et al. | |
| 2013/0116470 A1 | 5/2013 | Miura et al. | |
| 2013/0261334 A1 | 10/2013 | Shimizu et al. | |
| 2013/0264186 A1 | 10/2013 | Shimizu et al. | |
| 2013/0281735 A1 | 10/2013 | Shimizu et al. | |
| 2013/0303800 A1 | 11/2013 | Shimizu | |
| 2013/0310603 A1 | 11/2013 | Shimizu et al. | |
| 2014/0187812 A1 | 7/2014 | Wellman et al. | |
| 2015/0368176 A1 | 12/2015 | Miura et al. | |
| 2017/0260120 A1 | 9/2017 | Shimizu et al. | |
| 2017/0349521 A1 | 12/2017 | Shimizu et al. | |

FOREIGN PATENT DOCUMENTS

| | | |
|---|---|---|
| CN | 103121934 A | 5/2013 |
| EP | 0161874 B2 | 7/1992 |
| GB | 721301 A | 1/1955 |
| GB | 2112394 A | 7/1982 |
| JP | H0867650 A | 3/1996 |
| JP | H10231267 A | 9/1998 |
| JP | H11315046 A | 11/1999 |
| JP | 2001505199 A | 4/2001 |

OTHER PUBLICATIONS

Celanese, "Acetic Acid", Celanese—The chemistry inside innovation™, 2013. Brochure.

International Search Report received in the related International Patent Application No. PCT/US2016/061570, dated Jan. 31, 2017.

Title—"Control of propionic acid content in acetic acid production by carbonylation of methanol", Aug. 25, 2013, 20, pp. 50-52, p. 51, right column, line 4-13.

Title—"Control of formation of ethanol in methanol", Sep. 15, 2007, $5^{th}$ period, pp. 21-22, left column, lines 8-16.

Title—"A method to reduce ethanol content in purified methanol", Aug. 25, 2010, vol. 33, No. 4, pp. 225-227, p. 225, left column, line 2-9.

Title—"Purification of crude methanol", Jan. 15, 1997, 1997, $1^{st}$ period, pp. 1-5 and 11, p. 2, left column, line 24—right column, line 3.

Kirk-Othmer Encyclopedia of Chemical Technology $4^{th}$ Ed, Mass Transfer to Neuroregulators, a Wiley-Interscience publication; John Wiley & Sons, Inc., vol. 16, 1995, p. 554, lines 9-17.

Knopp, et al., "The Thermodynamics of the Thermal Decomposition of Acetic Acid in the Liquid Phase", J. Phys. Chem, 1962, pp. 1513-1516.

IMPCA Methanol Reference Specifications, International Methanol Producers & Consumers Association, Dec. 9, 2010, p. 1.

Title: "Specification of ethanol content of methanol products", May 15, 2008, 2008, $3^{rd}$ period, pp. 52-54, p. 53, left column, lines 14-20.

Title: "Consideration for four-column distillation process for methanol production", Sep. 20, 1998, 1998, $9^{th}$ period, pp. 21-22.

* cited by examiner

PROCESSES FOR PURIFYING ACETIC ACID AND HYDRATING ANHYDRIDE

CROSS-REFERENCES TO RELATED APPLICATIONS

This patent application is a continuation of U.S. application Ser. No. 16/165,575, filed Oct. 19, 2018, which is a continuation of U.S. application Ser. No. 15/863,484, filed Jan. 5, 2018, now U.S. Pat. No. 10,160,714, which is a continuation of U.S. application Ser. No. 15/348,466, filed on Nov. 10, 2016, now U.S. Pat. No. 9,908,835, which claims the priority of U.S. Application No. 62/255,060, filed Nov. 13, 2015, the disclosure of which is incorporated herein by reference in its entirety.

FIELD OF THE INVENTION

This invention relates to processes for producing acetic acid and, in particular, to improved processes for hydrating acetic anhydride in a product stream to form a purified acetic acid product comprising acetic anhydride at a concentration of no more than 50 wppm.

BACKGROUND OF THE INVENTION

Among currently employed processes for synthesizing acetic acid, one of the most useful commercially is the catalyzed carbonylation of methanol with carbon monoxide as taught in U.S. Pat. No. 3,769,329, incorporated herein by reference in its entirety. The carbonylation catalyst contains rhodium, either dissolved or otherwise dispersed in a liquid reaction medium or supported on an inert solid, along with a halogen-containing catalyst promoter as exemplified by methyl iodide. The rhodium can be introduced into the reaction system in any of many forms. Likewise, because the nature of the halide promoter is not generally critical, a large number of suitable promoters, most of which are organic iodides, may be used. Most typically and usefully, the reaction is conducted by continuously bubbling carbon monoxide gas through a liquid reaction medium in which the catalyst is dissolved.

A widely used and successful commercial process for synthesizing acetic acid involves the catalyzed carbonylation of methanol with carbon monoxide. The catalyst contains rhodium and/or iridium and a halogen promoter, typically methyl iodide. The reaction is conducted by continuously bubbling carbon monoxide through a liquid reaction medium in which the catalyst is dissolved. The reaction medium comprises acetic acid, methyl acetate, water, methyl iodide and the catalyst. Commercial processes for the carbonylation of methanol include those described in U.S. Pat. No. 3,769,329. Another conventional methanol carbonylation process includes the Cativa™ process, which is discussed in Jones, J. H. (2002), "*The Cativa™ Process for the Manufacture of Acetic Acid,*" Platinum Metals Review, 44 (3): 94-105, the entirety of which is incorporated herein by reference.

The AO™ process for the carbonylation of an alcohol to produce the carboxylic acid having one carbon atom more than the alcohol in the presence of a rhodium catalyst is disclosed in U.S. Pat. Nos. 5,001,259; 5,026,908; and 5,144,068; and EP0161874, the entireties of which are incorporated herein by reference. As disclosed therein, acetic acid is produced from methanol in a reaction medium containing methyl acetate (MeAc), methyl halide, especially methyl iodide (MeI), and rhodium present in a catalytically effective concentration. These patents disclose that catalyst stability and the productivity of the carbonylation reactor can be maintained at high levels, even at very low water concentrations, i.e., 4 weight percent or less, (despite the prior practice of maintaining approximately 14-15 wt. % water) by maintaining in the reaction medium, along with a catalytically effective amount of rhodium, at least a finite concentration of water, e.g., 0.1 wt. %, and a specified concentration of iodide ions over and above the iodide ion that is present as hydrogen iodide. This iodide ion is a simple salt, with lithium iodide being preferred. The salt may be formed in situ, for example, by adding lithium acetate, lithium carbonate, lithium hydroxide or other lithium salts of anions compatible with the reaction medium. The patents teach that the concentration of methyl acetate and iodide salts are significant parameters in affecting the rate of carbonylation of methanol to produce acetic acid, especially at low reactor water concentrations. By using relatively high concentrations of the methyl acetate and iodide salt, a high degree of catalyst stability and reactor productivity is achieved even when the liquid reaction medium contains water in finite concentrations as low as 0.1 wt. %. Furthermore, the reaction medium employed improves the stability of the rhodium catalyst, i.e., resistance to catalyst precipitation, especially during the product recovery steps of the process. In these steps, distillation for the purpose of recovering the acetic acid product tends to remove from the catalyst the carbon monoxide, which in the environment maintained in the reaction vessel, is a ligand with stabilizing effect on the rhodium.

U.S. Pat. No. 5,144,068 discloses a process for producing acetic acid by reacting methanol with carbon monoxide in a liquid reaction medium containing a rhodium (Rh) catalyst and comprising water, acetic acid, methyl iodide, and methyl acetate, wherein catalyst stability is maintained in the reaction by maintaining in said reaction medium during the course of said reaction 0.1 wt. % to 14 wt. % of water together with (a) an effective amount in the range of 2 wt. % to 20 wt. % of a catalyst stabilizer selected from the group consisting of iodide salts which are soluble in said reaction medium in effective concentration at reaction temperature, (b) 5 wt. % to 20 wt. % of methyl iodide, and (c) 0.5 wt. % to 30 wt. % of methyl acetate. Suitable iodide salts may be a quaternary iodide salt or an iodide salt of a member of the group consisting of the metals of Group IA and Group IIA of the Periodic Table.

Carbonyl impurities, such as acetaldehyde, that are formed during the carbonylation of methanol may react with iodide catalyst promoters to form multi-carbon alkyl iodides, e.g., ethyl iodide, propyl iodide, butyl iodide, pentyl iodide, hexyl iodide, and the like. It is desirable to remove multi-carbon alkyl iodides from the reaction product because even small amounts of these impurities in the acetic acid product tend to poison the catalyst used in the production of vinyl acetate, a product commonly produced from acetic acid.

Conventional techniques to remove such impurities include treating the crude acid product streams with oxidizers, ozone, water, methanol, activated-carbon, amines, and the like. Such treatments may or may not be combined with distillation of the acetic acid. The most typical purification treatment involves a series of distillations to yield a suitable purified acetic acid as the final product. It is also known to remove carbonyl impurities from organic streams by treating the organic streams with an amine compound such as hydroxylamine, which reacts with the carbonyl compounds to form oximes, followed by distillation to separate the purified organic product from the oxime reaction products. However, the additional treatment of the purified acetic acid adds cost to the process, and distillation of the treated acetic acid product can result in additional impurities being formed.

While it is possible to obtain acetic acid of relatively high purity, the acetic acid product formed by the low-water carbonylation process and purification treatment described above frequently remains somewhat deficient with respect to the permanganate time due to the presence of small proportions of residual impurities. Because a sufficient permanganate time is an important commercial test, which the acid product may be required to meet to be suitable for many uses, the presence of impurities that decrease permanganate time is objectionable. Moreover, it has not been economically or commercially feasible to remove minute quantities of these impurities from the acetic acid by distillation because some of the impurities have boiling points close to that of the acetic acid product or halogen-containing catalyst promoters, such as methyl iodide. It has thus become important to identify economically viable methods of removing impurities elsewhere in the carbonylation process without contaminating the purified acetic acid or adding unnecessary costs.

Macroreticulated or macroporous strong acid cationic exchange resin compositions are conventionally utilized to reduce iodide contamination. Suitable exchange resin compositions, e.g., the individual beads thereof, comprise both sites that are functionalized with a metal, e.g., silver, mercury or palladium, and sites that remain in the acid form. Exchange resin compositions that have little or no metal-functionality do not efficiently remove iodides and, as such, are not conventionally used to do so. Typically, metal-functionalized exchange resins are provided in a fixed bed and a stream comprising the crude acetic acid product is passed through the fixed resin bed. In the metal functionalized resin bed, the iodide contaminants contained in the crude acetic acid product are removed from the crude acid product stream.

Widely used and successful commercial processes for synthesizing acetic anhydride also involves the catalyzed carbonylation of methanol with carbon monoxide. Acetic anhydride processes have been disclosed in U.S. Pat. Nos. 5,292,948; 4,374,070; 4,115,444; and 4,046,807, the entireties of which are incorporated herein by reference.

Other ion exchange resins have been used to remove iodide impurities from acetic acid and/or acetic anhydride. U.S. Pat. No. 6,657,078 describes a low-water process that uses a metal-functionalized exchange resin to remove iodides. The reference also avoids the use of a heavy ends column, resulting in energy savings. U.S. Pat. No. 5,220,058 also discloses the use of ion exchange resins having metal exchanged thiol functional groups for removing iodide impurities from acetic acid and/or acetic anhydride. Typically, the thiol functionality of the ion exchange resin has been exchanged with silver, palladium, or mercury. U.S. Pat. No. 5,227,524 discloses a process for removing iodide derivatives from liquid acetic acid and/or acetic anhydride comprises contacting the liquid acetic acid and/or acetic anhydride with a strong acid cation exchange resin having from about 4% to about 12% crosslinking, a surface area in the proton exchanged form of less than 10 m$^2$g$^{-1}$ after drying from the water wet state and a surface area of greater than 10 m$^2$ g$^{-1}$ after drying from a wet state in which water has been replaced by methanol. The resin has at least one percent of its active sites converted to the silver form, preferably from 30 to 70 percent.

U.S. Pat. No. 5,801,279 discloses a method which can reduce the amount of silver or mercury dissolved in a solution after contact and can increase the usage of silver or mercury without installing new treating facilities in a process for removing iodine compounds contained in an organic medium, particularly acetic acid or a mixture of acetic acid or acetic anhydride, by contacting them with a cation exchange resin in which at least 1% of the active sites are converted to a silver form or a mercury form. This disclosed method is characterized by carrying out the operation while elevating the temperatures in stages while contacting the organic medium, particularly acetic acid or a mixture of acetic acid and acetic anhydride, containing the iodine compounds with a cation exchange resin.

U.S. Pat. No. 5,344,976 discloses that the metal ion contaminants in the acid and/or anhydride may arise from corrosion or the use of reagents in the upstream process. The patent describes the use of a cationic exchanger in the acid form to remove at least a portion of the metal ion contaminants such as iron, potassium, calcium, magnesium, and sodium from a carboxylic acid stream prior to contacting the stream with the exchanged strong acid cation exchange resin to remove $C_1$ to $C_{10}$ alkyl iodide compounds, hydrogen iodide or iodide salts.

U.S. Pat. No. 5,648,531 discloses a process for continuously producing acetic anhydride alone or acetic anhydride and acetic acid by reacting methyl acetate and/or dimethyl ether and, optionally, water and/or methanol, with carbon monoxide alone or carbon monoxide and hydrogen in the presence of a rhodium compound and methyl iodide as principal catalysts. Trace impurities causative of tar formation are distilled and separated in an evaporator and/or a subsequent refining step to remove the same. The removal of the trace impurities causative of tar formation serves to decrease the amount of tar formed as an impurity.

U.S. Pat. No. 8,759,576 discloses a process for purifying acetic anhydride. The process includes the steps of feeding a liquid crude acetic anhydride stream directly to a distillation column and separating the liquid crude acetic anhydride stream to produce a light ends stream, a sidedraw and a residue stream. The sidedraw comprises substantially pure acetic anhydride product. The distillation column is operated at a pressure less than 101 kPa. The substantially pure acetic anhydride product comprises greater than 98 wt. % acetic anhydride, has a permanganate time of greater than 10 minutes, and has an APHA color of less than 10.

While the above-described processes have been successful, the need exists for improved processes for producing acetic acid, in particular, for methods for removing acetic anhydride from those processes.

SUMMARY OF THE INVENTION

This invention generally relates to processes for the production of acetic acid. One embodiment of the present invention relates to a process for purifying acetic acid, comprising distilling a process stream in a column, the process stream comprising acetic acid at a concentration of greater than 90 wt. %, water at a concentration from 1 to 3 wt. %, one or more $C_1$-$C_{14}$ alkyl iodides in a total concentration of no more than 6 wt. %, and methyl acetate at a concentration of no more than 6 wt. %, forming acetic anhydride in a lower portion of the column, withdrawing a product stream from the lower portion of the column, the product stream comprising acetic acid, water at a concentration of no more than 0.2 wt. %, and acetic anhydride at a concentration of no more than 600 wppm, e.g., from 5 to 600 wppm, and hydrating the acetic anhydride in the product stream to form a purified acetic acid product comprising acetic anhydride at a concentration of no more than 50 wppm, e.g., from 0.5 to 50 wppm. Preferably, the acetic anhydride concentration in the purified acetic acid product is less than the acetic anhydride concentration in the product stream. In one embodiment, the water concentration is maintained at a concentration of no more than 0.2 wt. %. The hydrating step may reduce the acetic anhydride concentration by at least 60%. In one embodiment, the hydrating step comprises contacting the product stream with a cation exchange resin. The cation exchange resin may comprise sulfonic acid or partially metal impregnated sulfonic acid functional groups. In one embodiment, the product stream is not contacted with an aqueous stream after withdrawal of the product stream from the lower portion of the column. The process stream that is distilled is substantially free of acetic anhydride, e.g., the acetic anhydride concentrations are below detectable limits. In addition to acetic acid and water, the process stream may also comprise hydrogen iodide at a concentration of no more than 300 wppm. The product stream may be withdrawn at a point within 5 actual stages from the base of the column. The water concentration in the lower portion of the column is maintained to be less than the water concentration of the process stream. In further embodiments, the process comprises contacting the purified acetic acid product with a metal-exchanged ion exchange resin having acid cation exchange sites to reduce the iodide concentration of the purified acetic acid product to no more than 100 wppb.

In another embodiment, there is provided a process for purifying acetic acid comprising carbonylating, in a reactor, at least one member selected from the group consisting of methanol, dimethyl ether, and methyl acetate in a reaction medium comprising water at a concentration from 0.1 to 14 wt. %, a rhodium catalyst, methyl iodide, and an iodide salt, separating the reaction medium to form a liquid recycle stream and a vapor product stream, distilling at least a portion of the vapor product stream in a first column to obtain a side stream comprising acetic acid at a concentration greater than 90 wt. %, water at a concentration from 1 to 3 wt. %, one or more $C_1$-$C_{14}$ alkyl iodides in a total concentration of no more than 6 wt. % and methyl acetate at a concentration of no more than 6 wt. %, distilling the side stream in a second column to obtain a product stream comprising acetic acid, water at a concentration of no more than 0.2 wt. % and acetic anhydride at a concentration of no more than 600 wppm, e.g., from 10 to 600 wppm, and contacting the product stream with a cation exchange resin to form a purified acetic acid product comprising no more than 50 wppm acetic anhydride. In one embodiment, the production rate of acetic anhydride is greater in the second column than the reactor. The side stream is substantially free of acetic anhydride, e.g., the acetic anhydride concentrations are below detectable limits. The side stream may also comprise hydrogen iodide at a concentration of no more than 300 wppm. The purified acetic acid product may comprise water at a concentration of no more than 0.2 wt. % and acetic anhydride at a concentration of no more than 10 wppm. In one embodiment, the water concentration in a lower portion of the second column is maintained to be less than the water concentration of the side stream. The acetic anhydride concentration of the purified acetic acid product is less than the acetic anhydride concentration of the product stream. The cation exchange resin may reduce the acetic anhydride concentration of the product stream by at least 60%. In further embodiments, the process comprises contacting the purified acetic acid product with a metal-exchanged ion exchange resin having acid cation exchange sites to reduce the iodide concentration of the purified acetic acid product to no more than 100 wppb.

BRIEF DESCRIPTION OF THE DRAWINGS

The present invention will be better understood in view of the appended non-limiting figures, wherein.

DETAILED DESCRIPTION OF THE INVENTION

Figure 1:
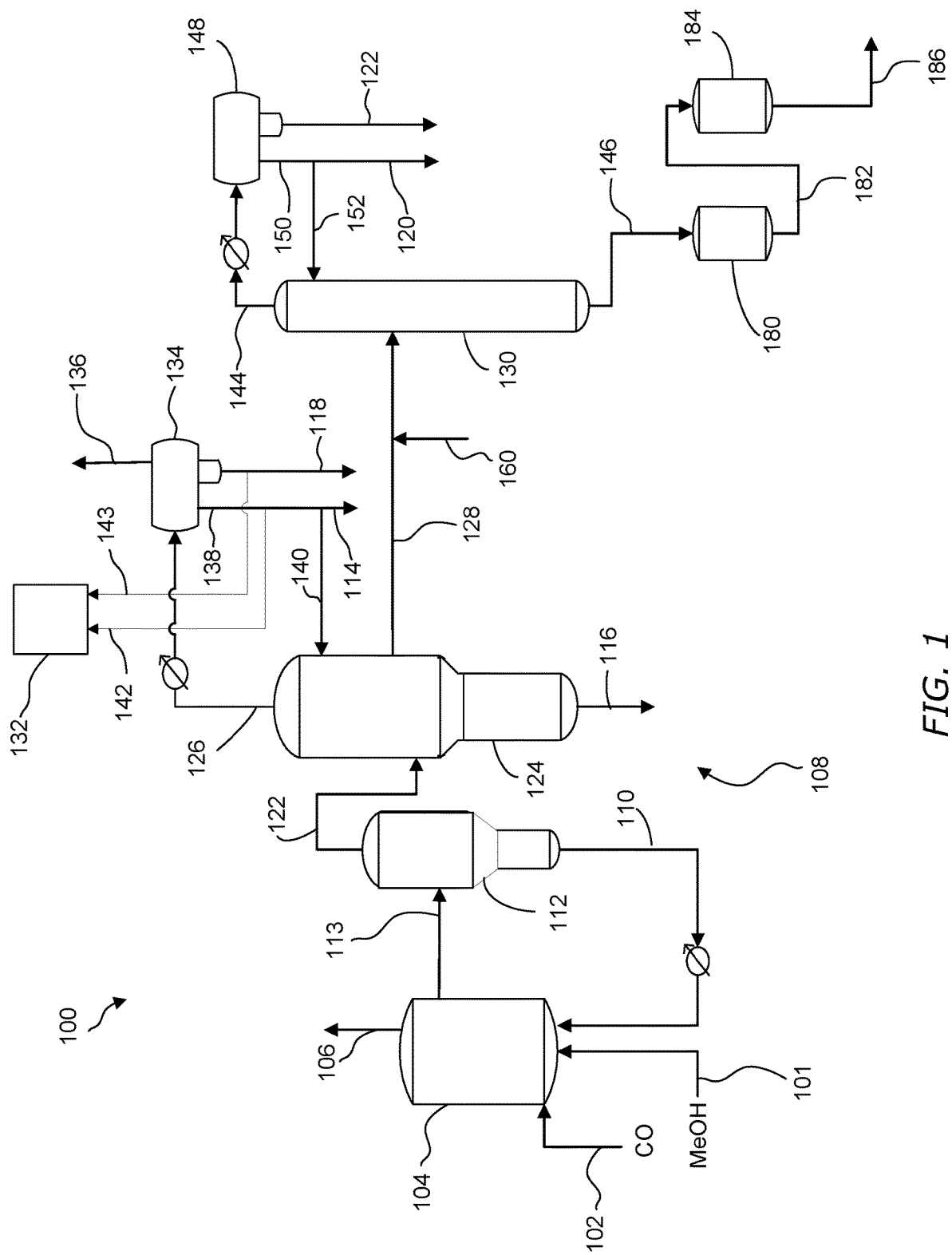
FIG. 1 illustrates a process for purifying acetic acid with cation exchange resin to hydrate acetic anhydride and a metal functionalized fixed resin bed for iodide removal.

At the outset, it should be noted that in the development of any such actual embodiment, numerous implementation—specific decisions must be made to achieve the developer's specific goals, such as compliance with system related and business related constraints, which will vary from one implementation to another. In addition, the processes disclosed herein can also comprise components other than those cited or specifically referred to, as is apparent to one having average or reasonable skill in the art.

In the summary and this detailed description, each numerical value should be read once as modified by the term "about" (unless already expressly so modified), and then read again as not so modified unless otherwise indicated in context. Also, in the summary and this detailed description, it should be understood that a concentration range listed or described as being useful, suitable, or the like, is intended that any and every concentration within the range, including the end points, is to be considered as having been stated. For example, a range "from 1 to 10" is to be read as indicating each and every possible number along the continuum between about 1 and about 10. Thus, even if specific data points within the range, or even no data points within the range, are explicitly identified or refer to only a few specific data points, it is to be understood that inventors appreciate and understand that any and all data points within the range are to be considered to have been specified, and that inventors possessed knowledge of the entire range and all points within the range.

Throughout the entire specification, including the claims, the following terms have the indicated meanings unless otherwise specified.

As used in the specification and claims, "near" is inclusive of "at." The term "and/or" refers to both the inclusive "and" case and the exclusive "or" case, and is used herein for brevity. For example, a mixture comprising acetic acid and/or methyl acetate may comprise acetic acid alone, methyl acetate alone, or both acetic acid and methyl acetate.

All percentages are expressed as weight percent (wt. %), based on the total weight of the particular stream or composition present, unless otherwise noted. Room temperature is 25° C. and atmospheric pressure is 101.325 kPa unless otherwise noted.

For purposes herein: acetic acid may be abbreviated as "AcOH"; acetaldehyde may be abbreviated as "AcH"; methyl acetate may be abbreviated "MeAc"; methanol may be abbreviated "MeOH"; methyl iodide may be abbreviated as "MeI"; hydrogen iodide may be abbreviated as "HI";

carbon monoxide may be abbreviated "CO"; and dimethyl ether may be abbreviated "DME".

HI refers to either molecular hydrogen iodide or dissociated hydriodic acid when at least partially ionized in a polar medium, typically a medium comprising at least some water. Unless otherwise specified, the two are referred to interchangeably. Unless otherwise specified, HI concentration is determined via acid-base titration using a potentiometric end point. In particular, HI concentration is determined via titration with a standard lithium acetate solution to a potentiometric end point. It is to be understood that for purposes herein, the concentration of HI is not determined by subtracting a concentration of iodide assumed to be associated with a measurement of corrosion metals or other non H+ cations from the total ionic iodide present in a sample.

It is to be understood that HI concentration does not refer to iodide ion concentration. HI concentration specifically refers to HI concentration as determined via potentiometric titration.

This subtraction method is an unreliable and imprecise method to determine relatively lower HI concentrations (i.e., less than about 5 weight percent) due to the fact that it assumes all non-H+ cations (such as cations of Fe, Ni, Cr, Mo) are associated with iodide anion exclusively. In reality, a significant portion of the metal cations in this process can be associated with acetate anion. Additionally, many of these metal cations have multiple valence states, which adds even more unreliability to the assumption on the amount of iodide anion which could be associated with these metals. Ultimately, this method gives rise to an unreliable determination of the actual HI concentration, especially in view of the ability to perform a simple titration directly representative of the HI concentration.

For purposes herein, an "overhead" or "distillate" of a distillation column refers to at least one of the lower boiling condensable fractions which exits at or near the top, (e.g., proximate to the top), of the distillation column, and/or the condensed form of that stream or composition. Obviously, all fractions are ultimately condensable, yet for purposes herein, a condensable fraction is condensable under the conditions present in the process as readily understood by one of skill in the art. Examples of noncondensable fractions may include nitrogen, hydrogen, and the like. Likewise, an overhead stream may be taken just below the upper most exit of a distillation column, for example, wherein the lowest boiling fraction is a non-condensable stream or represents a de-minimis stream, as would be readily understood by one of reasonable skill in the art.

The "bottoms" or "residuum" of a distillation column refers to one or more of the highest boiling fractions which exit at or near the bottom of the distillation column, also referred to herein as flowing from the bottom sump of the column. It is to be understood that a residuum may be taken from just above the very bottom exit of a distillation column, for example, wherein the very bottom fraction produced by the column is a salt, an unusable tar, a solid waste product, or a de-minimis stream as would be readily understood by one of reasonable skill in the art.

For purposes herein, distillation columns comprise a distillation zone and a bottom sump zone. The distillation zone includes everything above the bottom sump zone, i.e., between the bottom sump zone and the top of the column. For purposes herein, the bottom sump zone refers to the lower portion of the distillation column in which a liquid reservoir of the higher boiling components is present (e.g., the bottom of a distillation column) from which the bottom or residuum stream flows upon exiting the column. The bottom sump zone may include reboilers, control equipment, and the like.

It is to be understood that the term "passages," "flow paths," "flow conduits," and the like in relation to internal components of a distillation column are used interchangeably to refer to holes, tubes, channels, slits, drains, and the like, which are disposed through and/or which provide a path for liquid and/or vapor to move from one side of the internal component to the other side of the internal component. Examples of passages disposed through a structure such as a liquid distributor of a distillation column include drain holes, drain tubes, drain slits, and the like, which allow a liquid to flow through the structure from one side to another.

Average residence time is defined as the sum total of all liquid volume hold-up for a given phase within a distillation zone divided by the average flow rate of that phase through the distillation zone. The hold-up volume for a given phase can include liquid volume contained in the various internal components of the column including collectors, distributors and the like, as well as liquid contained on trays, within downcomers, and/or within structured or random packed bed sections.

Hydration of Acetic Anhydride

The present invention relates to processes for the purification of acetic acid and, in particular, to improved processes for hydrating acetic anhydride in a product stream comprising acetic acid, water at a concentration of no more than 0.2 wt. %, and acetic anhydride at a concentration of no more than 600 wppm. Advantageously, the disclosed embodiments provide a purified acetic acid product comprising acetic anhydride at a concentration of no more than 50 wppm, e.g., no more than 40 wppm, no more than 30 wppm, no more than 20 wppm, no more than 10 wppm or no more than 5 wppm. In terms of ranges, the purified acetic acid product comprises acetic anhydride at a concentration from 0.5 to 50 wppm, e.g., from 0.5 to 40 wppm, from 0.5 to 30 wppm, from 0.5 to 20 wppm, or from 0.5 to 10 wppm. The purified acetic acid product comprises less acetic anhydride than the product stream. This process yields a high quality purified acetic acid product that may be widely used in various applications.

During purification of acetic acid obtained by methanol carbonylation, one or more distillation columns may be used to separate impurities from the process stream and yield a purified product stream according to embodiments of the present invention. Typically, in one of the distillation columns, water is separated to yield a glacial acetic acid product having a water concentration of no more than 0.2 wt. %, e.g., no more than 0.15 wt. %, no more than 0.1 wt. %, or no more than 0.05 wt. %. It has been found that in the lower portion of this column, due to the substantially anhydrous conditions (no more than 0.2 wt. % water), acetic anhydride side reactions may occur, leading to acetic anhydride formation that contaminates the product stream. This may lead to deleterious acetic acid products that have quality control issues. Although acetic acid/acetic anhydride co-production may involve separating these components, it is not practical or efficient to separate acetic anhydride from the product stream using such methods. Advantageously, the present invention overcomes problems associated with the acetic anhydride contamination by hydrating the product to reduce and/or eliminate acetic anhydride.

In one embodiment, the process stream fed to the distillation columns is substantially free of acetic anhydride, meaning the acetic anhydride concentrations are below detectable limits. Detectable limits may detect acetic anhydride in concentration of greater than 0.5 wppm. Stated differently, the process stream is obtained from a methanol carbonylation process that produces acetic acid under aqueous conditions, e.g., in a reaction medium comprising water at a concentration of greater than 0.1 wt. %. Thus, the process stream is substantially free of acetic anhydride produced in the carbonylation reactor.

In one embodiment, there is provided a process for purifying acetic acid, comprising distilling a process stream in a column, the process stream comprising acetic acid and water, wherein the process stream is substantially free of acetic anhydride, forming acetic anhydride in a lower portion of the column, withdrawing a product stream from the lower portion of the column, the product stream comprising acetic acid, water at a concentration of no more than 0.2 wt. %, and acetic anhydride at a concentration of no more than 600 wppm, and hydrating the acetic anhydride in the product stream to form a purified acetic acid product comprising acetic anhydride at a concentration of no more than 50 wppm.

The process streams that are separated comprises acetic acid, water, and other components, such as, but not limited to methyl iodide, methyl acetate, hydrogen iodide, acetaldehyde, and propionic acid. Various process streams are disclosed herein. One exemplary process stream comprises acetic acid in amount of greater than or equal to 90 wt. %, e.g., greater than or equal to 94 wt. % or greater than or equal to 96 wt. %. The water concentration of the process stream may be in an amount from 1 to 3 wt. %, e.g., preferably from 1 to 2.5 wt. % and more preferably from 1.1 to 2.1 wt. %. The process stream may also comprise one or more $C_1$-$C_{14}$ alkyl iodides in a total concentration of no more than 6 wt. %, e.g., no more than 4 wt. %, or no more than 3.6 wt. %, and methyl acetate at a concentration of no more than 6 wt. %, e.g., no more than 4 wt. %, or no more than 3.6 wt. %. In some embodiments, in addition to acetic acid and water, the exemplary process stream may also comprise one or more $C_1$-$C_{14}$ alkyl iodides in an amount from 0.1 to 6 wt. %, e.g., from 0.5 to 5 wt. %, from 0.6 to 4 wt. %, from 0.7 to 3.7 wt. %, or from 0.8 to 3.6 wt. %. Generally, methyl iodide is the primary alkyl iodide and the concentration of the one or more $C_1$-$C_{14}$ alkyl iodides may be determined by the methyl iodide concentration. Due to the presence of water, the process stream may also contain methyl acetate in an amount from 0.1 to 6 wt. %, e.g., from 0.5 to 5 wt. %, from 0.6 to 4 wt. %, from 0.7 to 3.7 wt. %, or from 0.8 to 3.6 wt. %. In some embodiments, the process stream may also comprise hydrogen iodide at a concentration of no more than 300 wppm, e.g., or no more than 250 wppm, no more than 200 wppm, no more than 100 wppm, no more than 50 wppm, no more than 25 wppm, or no more than 10 wppm.

In one embodiment, there is provided a process for purifying acetic acid comprising distilling a process stream in a column, the process stream comprising acetic acid at a concentration greater than 90 wt. %, water at a concentration from 1 to 3 wt. %, one or more $C_1$-$C_{14}$ alkyl iodides in a total concentration of no more than 6 wt. % (from 0.1 to 6 wt. %), and methyl acetate at a concentration of no more than 6 wt. % (from 0.1 to 6 wt. %), and optionally hydrogen iodide at a concentration of no more than 300 wppm, forming acetic anhydride in a lower portion of the column, withdrawing a product stream from the lower portion of the column, the product stream comprising acetic acid, water at a concentration of no more than 0.2 wt. %, and acetic anhydride at a concentration of no more than 600 wppm, and hydrating the acetic anhydride in the product stream to form a purified acetic acid product comprising acetic anhydride at a concentration of no more than 50 wppm.

In one embodiment, the distillation column separates a process stream to yield a product stream comprising acetic acid, water, and acetic anhydride. The presence of acetic anhydride in the product stream is undesirable. In one embodiment, the product stream comprises acetic acid at a concentration of greater than or equal to 99.5 wt. %, e.g., greater than or equal to 99.7 wt. % or greater than or equal to 99.9 wt. %. The product stream comprises water at a concentration of no more than 0.2 wt. %, e.g., no more than 0.15 wt. %, no more than 0.1 wt. %, or no more than 0.05 wt. %. The product stream comprises a concentration of acetic anhydride that is undesirable and causes product quality issues. Even low amounts of acetic anhydride, e.g., amounts of 5 wppm, may contribute to product quality issues. In one embodiment, the product stream comprises acetic anhydride at a concentration of no more than 600 wppm, e.g., no more than 500 wppm, no more than 450 wppm, no more than 400 wppm, no more than 300 wppm, no more than 200 wppm, no more than 100 wppm, or no more than 50 wppm. In terms of ranges, the product stream comprises acetic anhydride in an amount from 5 to 600 wppm, e.g., from 10 to 600 wppm, from 5 to 450 wppm, from 10 to 450 wppm, from 10 to 300 wppm, or from 10 to 100 wppm. The embodiments of the present invention may also be used to reduce acetic anhydride in the product stream when the concentration exceeds 600 wppm. To treat these higher concentrations of acetic anhydride, the hydration may be repeated one or more times. Of course, if acetic anhydride is introduced into the column, the acetic anhydride may be higher than when it is not added, and the present invention may also remove the added acetic anhydride.

The product stream may be withdrawn from a location of a distillation column that yields a product stream having a water concentration that is less than the water concentration in the process stream. It has been found that in this portion of the distillation column, that even if no acetic anhydride is introduced into the column, acetic anhydride may be undesirably formed in the presence of substantially anhydrous conditions, e.g. no more than 0.2 wt. %. For example, the product stream may be withdrawn from the base of a distillation column or as a sidedraw from a lower portion of the distillation. In one embodiment, the sidedraw is withdrawn within 5 actual stages of the base, e.g., within 4 actual stages, within 3 actual stages, within 2 actual stages, within 1 actual stage, and preferably above the base of the second column. The second column may have from 10 to 80 actual states, e.g., from 15 to 80 actual stages or from 20 to 80 actual stages. An actual stage may correspond to a plate in a column. The sidedraw may be a liquid or vapor sidedraw.

In one embodiment, there is provided a process for purifying acetic acid, comprising distilling a process stream in a column, the process stream comprising acetic acid and water, wherein the process stream is substantially free of acetic anhydride, forming acetic anhydride in a lower portion of the column, withdrawing a product stream from the lower portion of the column, the product stream comprising acetic acid, water at a concentration of no more than 0.2 wt. %, and acetic anhydride at a concentration of no more than 600 wppm, and contacting the product stream with a cation exchange resin to hydrate the acetic anhydride in the product stream to form a purified acetic acid product comprising acetic anhydride at a concentration of no more than 50 wppm.

In one embodiment, the hydration of acetic anhydride may be conducted by contacting the product stream with a cation exchange resin. The product stream may be withdrawn from the distillation column contacted and with the cation exchange resin. Acetic anhydride is reacted in the cation exchange resin through a hydration reaction to convert the acetic anhydride into acetic acid. Because water has already been removed from the product stream, it is not desirable to increase the water concentration in the cation exchange resin. Thus, no aqueous streams are contacted with the product stream after withdrawal from the lower portion. In one embodiment, the water concentration in the cation exchange resin is maintained at or below the water concentration of the product stream, e.g., a water concentration of no more than 0.2 wt. %, e.g., no more than 0.15 wt. %, no more than 0.1 wt. %, or no more than 0.05 wt. %.

Suitable cation exchange resins for the hydration of acetic anhydride may comprise strong acid cation exchange resins, for example strong acid macroreticular or macroporous resins, for example Amberlyst® 15 resin (DOW), Purolite C145, or Purolite CT145. In one embodiment, the cation exchange resin comprises sulfonic acid or partially metal impregnated sulfonic acid functional groups. The resin may also be an acid-form strong acid cation exchange mesoporous resin. Chelating resins and zeolites may also be used.

Advantageously, by hydrating the product stream in the cation exchange resin, the acetic anhydride of the product stream may be reduced by at least 60%, e.g., at least 70%, at least 75%, at least 80%, or at least 85%. In one embodiment, the process for purifying acetic acid comprises distilling a process stream in a column, the process stream comprising acetic acid and water, forming acetic anhydride in a lower portion of the column, withdrawing a product stream from the lower portion, wherein the product stream comprises acetic anhydride, and hydrating the at least 60% of the acetic anhydride in the product stream to form a purified acetic acid product.

As disclosed further herein, the product stream may contain iodide in a concentration from 20 wppb to 1.5 wppm. The iodide may be removed by a metal ion-exchange resin. The metal-exchanged ion exchange resin can have at least 1% of the strong acid exchange sites occupied by silver, mercury, palladium, and/or rhodium, e.g., at least 2% silver, mercury, palladium, and/or rhodium, at least 5% silver, mercury, palladium, and/or rhodium, at least 10% silver, mercury, palladium, and/or rhodium, or at least 20% silver, mercury, palladium, and/or rhodium. The product stream have may an iodide content of greater than 100 wppb, e.g., greater than 100 wppb, greater than 200 wppb, greater than 400 wppb, greater than 500 wppb, or greater than 1000 wppb, prior to treatment with the metal ion-exchange resin and an iodide content of less than 10 wppb, e.g., less than 10 wppb, less than 7 wppb, less than 5 wppb, less than 3 wppb, less than 2 wppb, less than 1 wppb, after contacting the resin.

Cation Removal

Accordingly in one embodiment, the cation exchange resin for hydrating acetic anhydride is positioned upstream of the metal ion-exchange resin for removing iodides. This configuration may be desirable when, the cation exchange resin may also remove metal ion contaminants, in particular lithium cations, that cause displacement of the metals of the ion exchange resin. In one embodiment, the lithium cation in the product stream to be removed using the cation exchange resin may be derived from and/or generated by a compound in the reaction medium. In some embodiments, the cation exchange resin may remove cations may be selected from the group consisting of Groups IA and IIA of the periodic table, quaternary nitrogen cations, and phosphorous-containing cations. Higher alkyl iodides, $C_{10}$-$C_{14}$ alkyl iodides, may also be removed using the cation exchange resin.

In one embodiment, the cation exchange resin may also reduce lithium concentration in the product stream. Lithium has also been found to be entrained in the crude acid product in the absence of heavy ends and other finishing apparatus. Even very small amounts of lithium in the product stream, e.g., 10 wppb, may cause problems with removing iodides. Lithium may be present in the product stream as one or more lithium-containing compounds such as lithium iodide, lithium hydroxide, lithium acetate, lithium acetate dihydrate, lithium carbonate, lithium alkyl carbonate, methyl lithium, lithium chloride, or lithium oxalate. For purposes herein, the concentration of lithium-containing compound is reported as the concentration of the lithium in the lithium-containing compound. The product stream may comprise lithium in a concentration of up to or equal to 10 wppm, e.g., up to or equal to 5 wppm, up to or equal to 1 wppm, up to or equal to 500 wppb, up to or equal to 300 wppb, or up to or equal to 100 wppb. In terms of ranges, the crude acid product may comprise lithium in an amount from 0.01 wppm to 10 wppm, e.g., from 0.05 wppm to 5 wppm or from 0.05 wppm to 1 wppm. By utilizing a cationic exchanger in the acid form before introducing the crude acid product to a metal-exchanged resin, significant amounts of lithium can be removed. For example greater than or equal to 90 wt. % of the lithium in the stream may be removed by the cationic exchanger, e.g., greater than or equal to 92 wt. %, greater than or equal to 95 wt. %, greater than or equal to 98 wt. %, or greater than or equal to 99 wt. %. Thus, the stream exiting the acid-form cationic exchanger may contain no more than 50 wppb lithium, e.g., less than 25 wppb lithium, no more than 10 wppb, or no more than 5 wppb. Such removal of the lithium can greatly extend the life of the metal-exchanged resin.

In other embodiments, the lithium concentration in the product stream may be controlled by removing the product stream as a vapor sidedraw from the distillation column. When a vapor sidedraw is used, the product stream is condensed prior to contacting the cation exchange resin to hydrate the acetic anhydride and, optionally, remove cations.

In other embodiments, the cation exchange resin may be positioned downstream of the metal ion-exchange resin for removing iodides, or positioned in parallel with the metal ion-exchange resin for treating a portion of the product stream.

Acetic Acid Production Systems

An exemplary acetic acid production process is described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

In one embodiment, there is provided a process for producing acetic acid comprising carbonylating, in a reactor, at least one member selected from the group consisting of methanol, dimethyl ether, and methyl acetate in a reaction medium comprising water at a concentration from 0.1 to 14 wt. %, a rhodium catalyst, methyl iodide, and an iodide salt, separating the reaction medium to obtain a process stream comprising acetic acid and water, distilling the process stream in a column to obtain a product stream comprising acetic acid, water at a concentration of no more than 0.2 wt. % and acetic anhydride at a concentration of no more than 600 wppm and contacting the product stream with a cation exchange resin to form a purified acetic acid product comprising no more than 50 wppm acetic anhydride.

The purification processes described herein may be useful in carbonylation processes that use methanol and/or methyl acetate (MeAc), methyl formate or dimethyl ether, or mixtures thereof, to produce acetic acid in the presence of a Group VIII metal catalyst, such as rhodium, and a halogen-containing catalyst promoter. A particularly useful process is the low water rhodium-catalyzed carbonylation of methanol to acetic acid as exemplified in U.S. Pat. No. 5,001,259. Other metal catalysts, e.g., iridium-based catalysts, are contemplated as well.

Generally, the metal component, e.g., rhodium component, of the catalyst system is believed to be present in the form of a coordination compound of rhodium with a halogen component providing at least one of the ligands of such coordination compound. In addition to the coordination of rhodium and halogen, it is also believed that carbon monoxide coordinates with rhodium. The rhodium component of the catalyst system may be provided by introducing into the reaction zone rhodium in the form of rhodium metal, rhodium salts such as the oxides, acetates, iodides, carbonates, hydroxides, chlorides, etc., or other compounds that result in the formation of a coordination compound of rhodium in the reaction environment.

The metal catalyst may comprise a Group VIII metal. Suitable Group VIII catalysts include rhodium and/or iridium catalysts. When a rhodium catalyst is used, the rhodium catalyst may be added in any suitable form such that rhodium is in the catalyst solution as an equilibrium mixture including [Rh(CO)$_2$I$_2$]-anion, as is well known in the art. Iodide salts optionally maintained in the reaction mixtures of the processes described herein may be in the form of a soluble salt of an alkali metal or alkaline earth metal, quaternary ammonium, phosphonium salt or mixtures thereof. In certain embodiments, the catalyst co-promoter is lithium iodide, lithium acetate, or mixtures thereof. The salt co-promoter may be added as a non-iodide salt that generates an iodide salt. The iodide catalyst stabilizer may be introduced directly into the reaction system. Alternatively, the iodide salt may be generated in-situ since under the operating conditions of the reaction system, a wide range of non-iodide salt precursors reacts with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; 5,144,068 and 7,005,541, the entireties of which are hereby incorporated by reference. The carbonylation of methanol utilizing iridium catalyst is well known and is generally described in U.S. Pat. Nos. 5,942,460, 5,932,764, 5,883,295, 5,877,348, 5,877,347 and 5,696,284, the entireties of which are hereby incorporated by reference.

The halogen-containing catalyst promoter of the catalyst system consists of a halogen compound comprising an organic halide. Thus, alkyl, aryl, and substituted alkyl or aryl halides can be used. Preferably, the halogen-containing catalyst promoter is present in the form of an alkyl halide. Even more preferably, the halogen-containing catalyst promoter is present in the form of an alkyl halide in which the alkyl radical corresponds to the alkyl radical of the feed alcohol, which is being carbonylated. Thus, in the carbonylation of methanol to acetic acid, the halide promoter may include methyl halide, and more preferably methyl iodide.

The components of the reaction medium are maintained within defined limits to ensure sufficient production of acetic acid as the primary product and thus are not directed to co-production process for producing acetic acid along with a secondary product, such as acetic anhydride, in the reaction medium The reaction medium contains a concentration of the metal catalyst, e.g., rhodium catalyst, in an amount from 200 to 3000 wppm as rhodium, e.g., from 500 to 2000 wppm, or from 600 to 1500 wppm. The concentration of water in the reaction medium is maintained under low water conditions, e.g., water in amount of no more than 14 wt. %, from 0.1 wt. % to 14 wt. %, from 0.2 wt. % to 10 wt. % or most preferably from 0.25 wt. % to 5 wt. %. The concentration of methyl iodide in the reaction medium is maintained to be from 1 to 25 wt. %, e.g., from 5 to 20 wt. %, from 4 to 13.9 wt. %. The concentration of iodide salt, e.g., lithium iodide, in the reaction medium is maintained to be from 1 to 25 wt. %, e.g., from 2 to 20 wt. %, from 3 to 20 wt. %. The concentration of methyl acetate in the reaction medium is maintained to be from 0.5 to 30 wt. %, e.g., from 0.3 to 20 wt. %, from 0.6 to 4.1 wt. %. The concentration of acetic acid in the reaction medium is generally greater than or equal to 30 wt. %, e.g., greater than or equal to 40 wt. %, greater than or equal to 50 wt. %, or greater than or equal to 60 wt. %. Similar to the process stream disclosed herein, the reaction medium is substantially free of acetic anhydride. The following amounts are based on the total weight of the reaction medium.

In embodiments, the process for producing acetic acid further includes introducing a lithium compound into the reactor to maintain the concentration of lithium acetate in an amount from 0.3 to 0.7 wt. % in the reaction medium, wherein in an exemplary embodiment, in the reaction medium the concentration of the rhodium catalyst is maintained in an amount from 200 to 3000 wppm as rhodium in the reaction medium, the concentration of water is maintained in amount from 0.1 to 4.1 wt. % in the reaction medium, and the concentration of methyl acetate is maintained from 0.6 to 4.1 wt. % in the reaction medium, based on the total weight of the reaction medium present within the carbonylation reactor.

In embodiments, the lithium compound introduced into the reactor is selected from the group consisting of lithium acetate, lithium carboxylates, lithium carbonates, lithium hydroxide, other organic lithium salts, and mixtures thereof. In embodiments, the lithium compound is soluble in the reaction medium. In an embodiment, lithium acetate dihydrate may be used as the source of the lithium compound.

Lithium acetate reacts with hydrogen iodide according to the following equilibrium reaction (I) to form lithium iodide and acetic acid:

$$\text{LiOAc} + \text{HI} \rightleftharpoons \text{LiI} + \text{HOAc} \qquad (I)$$

Lithium acetate is thought to provide improved control of hydrogen iodide concentration relative to other acetates, such as methyl acetate, present in the reaction medium. Without being bound by theory, lithium acetate is a conjugate base of acetic acid and thus reactive toward hydrogen iodide via an acid-base reaction. This property is thought to result in an equilibrium of the reaction (I) which favors reaction products over and above that produced by the corresponding equilibrium of methyl acetate and hydrogen iodide. This improved equilibrium is favored by water concentrations of less than 4.1 wt. % in the reaction medium. In addition, the relatively low volatility of lithium acetate compared to methyl acetate allows the lithium acetate to remain in the reaction medium except for volatility losses and small amounts of entrainment into the vapor crude product. In contrast, the relatively high volatility of methyl acetate allows the material to distill into the purification train, rendering methyl acetate more difficult to control. Lithium acetate is much easier to maintain and control in the process at consistent low concentrations of hydrogen iodide. Accordingly, a relatively small amount of lithium acetate may be employed relative to the amount of methyl acetate needed to control hydrogen iodide concentrations in the reaction medium. It has further been discovered that lithium acetate is at least three times more effective than methyl acetate in promoting methyl iodide oxidative addition to the rhodium [I] complex. However, it has been discovered that lithium cations derived from and/or generated by the lithium compound in the reaction medium may be entrained or be volatile enough to concentrate with the crude acetic acid product after purification in the primary purification trains.

In embodiments, the concentration of lithium acetate in the reaction medium is maintained at greater than or equal to 0.3 wt. %, or greater than or equal to 0.35 wt. %, or greater than or equal to 0.4 wt. %, or greater than or equal to 0.45 wt. %, or greater than or equal to 0.5 wt. %, and/or in embodiments, the concentration of lithium acetate in the reaction medium is maintained at no more than 0.7 wt. %, or no more than 0.65 wt. %, or no more than 0.6 wt. %, or no more than 0.55 wt. %.

It has been discovered that an excess of lithium acetate in the reaction medium can adversely affect the other compounds in the reaction medium, leading to decrease productivity. Conversely, it has been discovered that a lithium acetate concentration in the reaction medium below about 0.3 wt. % is unable to maintain the desired hydrogen iodide concentrations in the reaction medium of below 1.3 wt. %.

In embodiments, the lithium compound may be introduced continuously or intermittently into the reaction medium. In embodiments, the lithium compound is introduced during reactor start up. In embodiments, the lithium compound is introduced intermittently to replace entrainment losses.

Thus, in one embodiment, there is provided a process for producing acetic acid comprising carbonylating, in a reactor, at least one member selected from the group consisting of methanol, dimethyl ether, and methyl acetate in a reaction medium comprising water at a concentration from 0.1 to 14 wt. %, a rhodium catalyst, methyl iodide, an iodide salt, and lithium acetate, separating the reaction medium to obtain a process stream comprising acetic acid and water, distilling the process stream in a column to obtain a product stream comprising acetic acid, water at a concentration of no more than 0.2 wt. % and acetic anhydride at a concentration of no more than 600 wppm and contacting the product stream with a cation exchange resin to form a purified acetic acid product comprising no more than 50 wppm acetic anhydride.

In some embodiments, the desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. A desired ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters.

The carbonylation reaction of methanol to acetic acid product may be carried out by contacting the methanol feed with gaseous carbon monoxide bubbled through an acetic acid solvent reaction medium containing the rhodium catalyst, methyl iodide promoter, methyl acetate, and additional soluble iodide salt, at conditions of temperature and pressure suitable to form the carbonylation product. It will be generally recognized that it is the concentration of iodide ion in the catalyst system that is important and not the cation associated with the iodide, and that at a given molar concentration of iodide the nature of the cation is not as significant as the effect of the iodide concentration. Any metal iodide salt, or any iodide salt of any organic cation, or other cations such as those based on amine or phosphine compounds (optionally, ternary or quaternary cations), can be maintained in the reaction medium provided that the salt is sufficiently soluble in the reaction medium to provide the desired level of the iodide. When the iodide is a metal salt, preferably it is an iodide salt of a member of the group consisting of the metals of Group IA and Group IIA of the periodic table as set forth in the "Handbook of Chemistry and Physics" published by CRC Press, Cleveland, Ohio, 2002-03 (83rd edition). In particular, alkali metal iodides are useful, with lithium iodide being particularly suitable. In the low water carbonylation process, the additional iodide ion over and above the iodide ion present as hydrogen iodide is generally present in the catalyst solution in amounts such that the total iodide ion concentration is from 1 to 25 wt. % and the methyl acetate is generally present in amounts from 0.5 to 30 wt. %, and the methyl iodide is generally present in amounts from 1 to 25 wt. %. The rhodium catalyst is generally present in amounts from 200 to 3000 wppm as rhodium.

The reaction medium may also contain impurities that should be controlled to avoid byproduct formation. One impurity in the reaction medium may be ethyl iodide, which is difficult to separate from acetic acid. Applicant has further discovered that the formation of ethyl iodide may be affected by numerous variables, including the concentration of acetaldehyde, ethyl acetate, methyl acetate and methyl iodide in the reaction medium. Additionally, ethanol content in the methanol source, hydrogen partial pressure and hydrogen content in the carbon monoxide source have been discovered to affect ethyl iodide concentration in the reaction medium and, consequently, propionic acid concentration in the final acetic acid product.

In embodiments, the propionic acid concentration in the acetic acid product may further be maintained below 250 wppm by maintaining the ethyl iodide concentration in the reaction medium at no more than 750 wppm without removing propionic acid from the acetic acid product.

In embodiments, the ethyl iodide concentration in the reaction medium and propionic acid in the acetic acid product may be present in a weight ratio from 3:1 to 1:2. In embodiments, the acetaldehyde:ethyl iodide concentration in the reaction medium is maintained at a weight ratio from 2:1 to 20:1.

In embodiments, the ethyl iodide concentration in the reaction medium may be maintained by controlling at least one of the hydrogen partial pressure, the methyl acetate concentration, the methyl iodide concentration, and/or the acetaldehyde concentration in the reaction medium.

In embodiments, the concentration of ethyl iodide in the reaction medium is maintained/controlled to be no more than 750 wppm, or e.g., no more than 650 wppm, or no more than 550 wppm, or no more than 450 wppm, or no more than 350 wppm. In embodiments, the concentration of ethyl iodide in the reaction medium is maintained/controlled at greater than or equal to 1 wppm, or e.g., 5 wppm, or 10 wppm, or 20 wppm, or 25 wppm, and no more than 650 wppm, or e.g., 550 wppm, or 450 wppm, or 350 wppm.

In embodiments, the weight ratio of ethyl iodide in the reaction medium to propionic acid in the acetic acid product may range from 3:1 to 1:2, or e.g., from 5:2 to 1:2, or from 2:1 to 1:2, or from 3:2 to 1:2.

In embodiments, the weight ratio of acetaldehyde to ethyl iodide in the reaction medium may range from 20:1 to 2:1, or e.g., from 15:1 to 2:1, from 9:1 to 2:1, or from 6:1.

Carbonylation Reaction

Typical reaction temperatures for carbonylation may be from 150 to 250° C., e.g., 160 to 240° C., 170-230° C. with the temperature range of 180 to 225° C. being a preferred range. The carbon monoxide partial pressure in the reactor can vary widely but is typically from 2 to 30 atm, e.g., from 3 to 10 atm. The hydrogen partial pressure in the reactor is typically from 0.05 to 2 atm, e.g., from 1 to 1.9 atm. Some embodiments of the present invention may be operated with a hydrogen partial pressure from 0.3 to 2 atm, e.g., from 0.3 to 1.5 atm, or from 0.4 to 1.5 atm. Because of the partial pressure of by-products and the vapor pressure of the contained liquids, the total reactor pressure may range from 15 to 40 atm. The production rate of acetic acid may be from 5 to 50 mol/L·h, e.g., from 10 to 40 mol/L·h, and preferably 15 to 35 mol/L·h. As indicated herein, the carbonylation reaction is conducted under conditions that do not produce acetic anhydride.

Exemplary reaction and acetic acid recovery system 100 is shown in FIG. 1. As shown, methanol-containing feed stream 101 and carbon monoxide-containing feed stream 102 are directed to liquid phase carbonylation reactor 104, in which the carbonylation reaction occurs to form acetic acid.

Carbonylation reactor 104 is preferably either a stirred vessel or bubble-column type vessel, with or without an agitator, within which the reacting liquid or slurry contents are maintained, preferably automatically, a predetermined level, which preferably remains substantially constant during normal operation. Into carbonylation reactor 104, fresh methanol, carbon monoxide, and sufficient water are continuously introduced as needed to maintain suitable concentrations in the reaction medium.

In a typical carbonylation process, carbon monoxide is continuously introduced into the carbonylation reactor, desirably below the agitator, which may be used to stir the contents. The gaseous feed preferably is thoroughly dispersed through the reacting liquid by this stirring means. Gaseous purge stream 106 desirably is vented from the reactor 104 to prevent buildup of gaseous by-products and to maintain a set carbon monoxide partial pressure at a given total reactor pressure. In one embodiment, the gaseous purge stream 106 contains low amounts of hydrogen iodide of no more than 1 wt. %, e.g., no more than 0.9 wt. %, no more than 0.8 wt. %, no more than 0.7 wt. %, no more than 0.5 wt. %, no more than 0.3 wt. %. Hydrogen iodide in excess of these amounts may increase the duty on the scrubber to prevent hydrogen iodide from being purged. The temperature of the reactor may be controlled and the carbon monoxide feed is introduced at a rate sufficient to maintain the desired total reactor pressure. Stream 113 comprising the liquid reaction medium exits reactor 104.

The acetic acid production system preferably includes primary purification train 108 employed to recover the acetic acid and recycle catalyst solution, methyl iodide, methyl acetate, and other system components within the process. Primary purification train 108 include light ends column 124 and drying column 130, and the associated pumps, overhead receivers, condensers, etc. Thus, a recycled catalyst solution, such as stream 110 from flash vessel 112, and optionally one or more of recycle streams 114, 116, 118, and 120, also are introduced into the reactor 104. Of course, one or more of the recycle streams may be combined prior to being introduced into the reactor. The separation system also preferably controls water and acetic acid content in the carbonylation reactor, as well as throughout the system, and facilitates PRC removal.

Flash Vessel

The reaction medium is drawn off from the carbonylation reactor 104 at a rate sufficient to maintain a constant level therein and is provided to flash vessel 112 via stream 113. In flash vessel 112, the crude product is separated in a flash separation step to obtain a vapor product stream 122 comprising acetic acid and less volatile stream 110, e.g., a liquid recycle stream, comprising a catalyst-containing solution (predominantly acetic acid containing the rhodium and the iodide salt along with lesser quantities of methyl acetate, methyl iodide, and water), which preferably is recycled to the reactor, as discussed above. The vapor product stream 122 also comprises methyl iodide, methyl acetate, water, and permanganate reducing compounds (PRC's). Dissolved gases exiting the reactor and entering the flash vessel comprise a portion of the carbon monoxide and may also contain gaseous by-products such as methane, hydrogen, and carbon dioxide. Such dissolved gases exit the flash vessel as part of the overhead stream.

In one embodiment, vapor product stream 122 comprises acetic acid, methyl iodide, methyl acetate, water, acetaldehyde, and hydrogen iodide. In one embodiment, vapor product stream 122 comprises acetic acid in an amount from 45 to 75 wt. %, methyl iodide in an amount from 20 to 50 wt. %, methyl acetate in an amount of no more than 9 wt. %, and water in an amount of no more than 15 wt. %, based on the total weight of the vapor product stream. In another embodiment, vapor product stream 122 comprises acetic acid in an amount from 45 to 75 wt. %, methyl iodide in an amount from 24 to less than 36 wt. %, methyl acetate in an amount of no more than 9 wt. %, and water in an amount of no more than 15 wt. %, based on the total weight of the vapor product stream. More preferably, vapor product stream 122 comprises acetic acid in an amount from 55 to 75 wt. %, methyl iodide in an amount from 24 to 35 wt. %, methyl acetate in an amount from 0.5 to 8 wt. %, and water in an amount from 0.5 to 14 wt. %. In yet a further preferred embodiment, vapor product stream 112 comprises acetic acid in an amount from 60 to 70 wt. %, methyl iodide in an amount from 25 to 35 wt. %, methyl acetate in an amount from 0.5 to 6.5 wt. %, and water in an amount from 1 to 8 wt. %. The acetaldehyde concentration in the vapor product stream may be in an amount from 0.005 to 1 wt. %, based on the total weight of the vapor product stream, e.g., from 0.01 to 0.8 wt. %, or from 0.01 to 0.7 wt. %. In some embodiments the acetaldehyde may be present in amounts no more than 0.01 wt. %. Vapor product stream 122 may comprise hydrogen iodide in an amount no more than 1 wt. %, based on the total weight of the vapor product stream, e.g., no more than 0.5 wt. %, or no more than 0.1 wt. %. Vapor product stream 122 is preferably substantially free of, i.e., contains no more than 0.0001 wt. %, propionic acid, based on the total weight of the vapor product stream. Similar to the process stream disclosed herein, vapor product stream 122 is substantially free of acetic anhydride.

Less volatile stream 110 comprises acetic acid, the metal catalyst, corrosion metals, as well as other various compounds. In one embodiment, liquid recycle stream comprises acetic acid in an amount from 60 to 90 wt. %, metal catalyst in an amount from 0.01 to 0.5 wt. %; corrosion metals (e.g., nickel, iron and chromium) in a total amount from 10 to 2500 wppm; lithium iodide in an amount from 5 to 20 wt. %; methyl iodide in an amount from 0.5 to 5 wt. %; methyl acetate in an amount from 0.1 to 5 wt. %; water in an amount from 0.1 to 8 wt. %; acetaldehyde in an amount of no more than 1 wt. % (e.g., from 0.0001 to 1 wt. % acetaldehyde); and hydrogen iodide in an amount of no more than 0.5 wt. % (e.g., from 0.0001 to 0.5 wt. % hydrogen iodide).

Recovery of Acetic Acid

The distillation and recovery of acetic acid is not particularly limited for the purposes of the present invention. In one embodiment, the process involves carbonylating, in a reactor, at least one member selected from the group consisting of methanol, dimethyl ether, and methyl acetate in a reaction medium comprising water at a concentration from 0.1 to 14 wt. %, a rhodium catalyst, methyl iodide, and an iodide salt, separating the reaction medium to form a liquid recycle stream and a vapor product stream, distilling at least a portion of the vapor product stream in a first column to obtain a side stream comprising acetic acid at a concentration greater than 90 wt. %, water at a concentration from 1 to 3 wt. %, one or more $C_1$-$C_{14}$ alkyl iodides in a total concentration of no more than 6 wt. % and methyl acetate at a concentration of no more than 6 wt. %, distilling the side stream in a second column to obtain a product stream comprising acetic acid, water at a concentration of no more than 0.2 wt. % and acetic anhydride at a concentration of no more than 600 wppm, and contacting the product stream with a cation exchange resin to form a purified acetic acid product comprising no more than 50 wppm acetic anhydride. Various embodiments of primary purification train having up to 2 distillation columns is further described herein.

First Column

For purposes of the present invention a process stream refers to any stream that is fed to the distillation column. In one embodiment vapor product stream 122 may be a process stream. The overhead stream from flash vessel 112 is directed to the light ends column 124 (first column) as vapor product stream 122, where distillation yields a low-boiling overhead vapor stream 126, a sidedraw 128 that contains acetic acid, and a high boiling residue stream 116. In one embodiment, vapor product stream 122 may comprise acetic acid, methyl acetate, water, methyl iodide, and acetaldehyde, along with other impurities such as hydrogen iodide and crotonaldehyde, and byproducts such as propionic acid. Acetic acid removed via sidedraw 128 preferably is subjected to further purification, such as in drying column 130 (second column) for selective separation of acetic acid from water as described further herein.

In one embodiment, sidedraw 128 is removed from a location above the feed of vapor product stream 122 to light ends column 124. Thus, acetic anhydride does not form because the water concentrations in that location of light ends column 124 at greater than 0.2 wt. %, greater than 0.5 wt. %, or greater than 1 wt. %.

Light ends column 124 also preferably forms residuum or bottoms stream 116, which comprises primarily acetic acid and water. Since light ends bottoms stream 116 typically comprises some residual catalyst, it may be beneficial to recycle all or a portion of light ends bottoms stream 116 to reactor 104. Optionally, light ends bottoms stream 116 may be combined with the catalyst phase 110 from flash vessel 112 and returned together to reactor 104, as shown in FIG. 1. Although the concentration of acetic acid may be relatively high in high boiling residue stream 116, the mass flow of the high boiling residue stream 116 relative to side stream 128 is very small. In embodiments, the mass flow of the boiling residue stream 116 is no more than 0.75% of side stream 128, e.g., no more than 0.55%, or no more than 0.45%.

In one embodiment, low-boiling overhead vapor stream 126 comprises water in amount greater than or equal to 5 wt. %, e.g., greater than or equal to 10 wt. %, or greater than or equal to 25 wt. %. The amount of water may be up to 80 wt. %. In terms of ranges, water concentration in the overhead may be from 5 wt. % to 80 wt. %, e.g., from 10 wt. % to 70 wt. % or from 25 wt. % to 60 wt. %. Reducing water concentration to less than 5 wt. % is not advantageous because this results in a large recycle of acetic acid back to the reaction system which then sets up a large recycle through the entire purification system. In addition to water, low-boiling overhead vapor stream 126 may also comprise methyl acetate, methyl iodide, and carbonyl impurities, which are preferably concentrated in the overhead to be removed from acetic acid in side stream 128. These carbonyl impurities may also be referred to herein as PRC's.

As shown, low-boiling overhead vapor stream 126 preferably is condensed and directed to an overhead phase separation unit, as shown by overhead decanter 134. Conditions are desirably maintained such that the condensed low-boiling overhead vapor stream 126, once in decanter 134, may separate to form a light liquid phase 138 and a heavy liquid phase 118. The phase separation should be maintain two separate phase, without forming a third phase or emulsion between the phases. An offgas component may be vented via line 136 from decanter 134. In embodiments, the average residence time of the condensed low-boiling overhead vapor stream 126 in overhead decanter 134 is greater than or equal to 1 minute, e.g., greater than or equal to 3 minutes, greater than or equal to 5 minutes, greater than or equal to 10 minutes, and/or the average residence time is no more than 60 minutes, e.g., no more than 45 minutes, or no more than 30 minutes, or no more than 25 minutes.

Although the specific compositions of the light phase stream 138 may vary widely, some preferred compositions are provided below in Table 1.

TABLE 1

| Exemplary Light Liquid Phase from Light Ends Overhead | | | |
|---|---|---|---|
| | conc. (Wt. %) | conc. (Wt. %) | conc. (Wt. %) |
| HOAc | 1-40 | 1-25 | 5-15 |
| Water | 50-90 | 50-80 | 60-80 |
| PRC's | <5 | <3 | <1 |
| MeI | <10 | <5 | <3 |
| MeAc | 1-50 | 1-25 | 1-15 |

In one embodiment, overhead decanter 134 is arranged and constructed to maintain a low interface level to prevent an excess hold up of methyl iodide. Although the specific compositions of heavy liquid phase 118 may vary widely, some exemplary compositions are provided below in Table 2.

TABLE 2

Exemplary Heavy Liquid Phase from Light Ends Overhead

|  | conc. (Wt. %) | conc. (Wt. %) | conc. (Wt. %) |
| --- | --- | --- | --- |
| Water | 0.01-2 | 0.05-1 | 0.1-0.9 |
| Methyl Acetate | 0.1-25 | 0.5-20 | 0.7-15 |
| Acetic Acid | 0.1-10 | 0.2-8 | 0.5-6 |
| PRC's | <5 | <3 | <1 |
| Methyl Iodide | 40-98 | 50-95 | 60-85 |

The density of the heavy liquid phase 118 may be from 1.3 to 2, e.g., from 1.5 to 1.8, from 1.5 to 1.75 or from 1.55 to 1.7. As described in U.S. Pat. No. 6,677,480, the measured density in the heavy liquid phase 118 correlates with the methyl acetate concentration in the reaction medium. As density decreases, the methyl acetate concentration in the reaction medium increases. In one embodiment of the present invention heavy liquid phase 118 is recycled to the reactor and the light liquid phase 138 is controlled to be recycled through the same pump. It may be desirable to recycle a portion of the light liquid phase 138 that does not disrupt the pump and maintains a density of the combined light liquid phase 138 and heavy liquid phase of greater than or equal to 1.3, e.g., greater than or equal to 1.4, greater than or equal to 1.5, or greater than or equal to 1.7. As described herein, a portion of the heavy liquid phase 118 may be treated to remove impurities such as acetaldehyde.

As shown in FIG. 1, the light phase exits decanter 134 via stream 138. A first portion, e.g., aliquot portion, of light phase stream 138 is recycled to the top of the light ends column 124 as reflux stream 140. In other embodiments a portion of the heavy liquid phase 118 may also be refluxed (not shown) to the light ends column 124.

PRC Removal System

As described herein the light ends column 124 is part of the primary purification train. In some embodiments, a portion of light liquid phase and/or heavy liquid phase may be separated and directed to acetaldehyde or PRC removal system 132 to recover methyl iodide and methyl acetate, while removing acetaldehyde. For purposes of the present invention, the acetaldehyde or PRC removal system 132 is not part of the primary purification train.

As shown in Tables 1 and 2, light liquid phase 133 and/or heavy liquid phase 118 each contain PRC's and the process may include removing carbonyl impurities, such as acetaldehyde, that deteriorate the quality of the acetic acid product and may be removed in suitable impurity removal columns and absorbers as described in U.S. Pat. Nos. 6,143,930; 6,339,171; 7,223,883; 7,223,886; 7,855,306; 7,884,237; 8,889,904; and US Pub. Nos. 2006/0011462, which are incorporated herein by reference in their entirety. Carbonyl impurities, such as acetaldehyde, may react with iodide catalyst promoters to form alkyl iodides, e.g., ethyl iodide, propyl iodide, butyl iodide, pentyl iodide, hexyl iodide, etc. Also, because many impurities originate with acetaldehyde, it is desirable to remove carbonyl impurities from the liquid light phase.

The portion of light liquid phase 138 and/or heavy liquid phase 118 fed to the acetaldehyde or PRC removal system 132 via lines 142 and 143, respectively, may vary from 1% to 99% of the mass flow of either the light liquid phase 138 and/or heavy liquid phase 118, e.g., from 1 to 50%, from 2 to 45%, from 5 to 40%, 5 to 30% or 5 to 20%. Also in some embodiments, a portion of both the light liquid phase 138 and heavy liquid phase 118 may be fed to the acetaldehyde or PRC removal system 132. The portion of the light liquid phase 138 not fed to the acetaldehyde or PRC removal system 132 may be refluxed to the first column or recycled to the reactor, as described herein. The portion of the heavy liquid phase 118 not fed to the acetaldehyde or PRC removal system 132 may be recycled to the reactor. Although a portion of heavy liquid phase 118 may be refluxed to the light ends column, it is more desirable to return the methyl iodide enriched heavy liquid phase 118 to the reactor.

In one embodiment, a portion of light liquid phase 138 and/or heavy liquid phase 118 is fed to a distillation column which enriches the overhead thereof to have acetaldehyde and methyl iodide. Depending on the configuration, there may be two separate distillation columns, and the overhead of the second column may be enriched in acetaldehyde and methyl iodide. Dimethyl ether, which may be formed in-situ, may also be present in the overhead. The overhead may be subject to one or more extraction stages to remove a raffinate enriched in methyl iodide and an extractant. A portion of the raffinate may be returned to the distillation column, first column, overhead decanter and/or reactor. For example, when the heavy liquid phase 118 is treated in the PRC removal system 132, it may be desirable to return a portion the raffinate to either the distillation column or reactor. Also, for example, when light liquid phase 138 is treated in the PRC removal system 132, it may be desirable to return a portion the raffinate to either the first column, overhead decanter, or reactor. In some embodiments, the extractant may be further distilled to remove water, which is returned to the one or more extraction stages. The column bottoms, which contains more methyl acetate and methyl iodide than light liquid phase 138, may also be recycled to reactor 104 and/or refluxed to light ends column 124.

Drying Column

Returning to the primary purification train, in addition to the overhead phase, the light ends column 124 also forms an acetic acid sidedraw 128, which preferably comprises primarily acetic acid and water, and is substantially free of acetic anhydride. In one embodiment, acetic acid sidedraw 128 is a process stream. In one embodiment, acetic acid sidedraw 128 comprises acetic acid in amount of greater than or equal to 90 wt. %, e.g., greater than or equal to 94 wt. % or greater than or equal to 96 wt. %. The water concentration of the process stream may be in an amount from 1 to 3 wt. %, e.g., from 1 to 2.5 wt. % and more preferably from 1.1 to 2.1 wt. %. The acetic acid sidedraw 128 may also comprise one or more $C_1$-$C_{14}$ alkyl iodides in a total concentration of no more than 6 wt. %, e.g., no more than 4 wt. %, or no more than 3.6 wt. %, and methyl acetate at a concentration of no more than 6 wt. %, e.g., no more than 4 wt. %, or no more than 3.6 wt. %. In some embodiments, in addition to acetic acid and water, acetic acid sidedraw 128 may also comprise one or more $C_1$-$C_{14}$ alkyl iodides in an amount from 0.1 to 6 wt. %, e.g., from 0.5 to 5 wt. %, from 0.6 to 4 wt. %, from 0.7 to 3.7 wt. %, or from 0.8 to 3.6 wt. %. Due to the presence of water, acetic acid sidedraw 128 may also contain methyl acetate in an amount from 0.1 to 6 wt. %, e.g., from 0.5 to 5 wt. %, from 0.6 to 4 wt. %, from 0.7 to 3.7 wt. %, or from 0.8 to 3.6 wt. %. In some embodiments, acetic acid sidedraw 128 may also comprise hydrogen iodide at a concentration of no more than 300 wppm, e.g., or no more than 250 wppm, no more than 200 wppm, no more than 100 wppm, no more than 50 wppm, no more than 25 wppm, or no more than 10 wppm.

In one embodiment, to maintain an efficient product separation, it is highly desired that the composition of the sidedraw 128 does not vary or fluctuate significantly during normal operation. By does not vary or fluctuate significantly it is meant that the concentration of the one or more $C_1$-$C_{14}$ alkyl iodides and the concentration of methyl acetate is ±0.9% of the water concentration in the side stream, e.g., ±0.7%, ±0.5%, ±0.4%, ±0.3%, ±0.2%, or ±0.1%. The water concentration in the side stream may be from 1 to 3 wt. %, e.g., preferably from 1.1 to 2.5 wt. %. For example, when the water concentration is 2.5 wt. %, the concentration of $C_1$-$C_{14}$ alkyl iodides is from 1.6 to 3.4 wt. %, and the concentration of methyl acetate is from 1.6 to 3.4 wt. %.

Optionally, a portion of the sidedraw 128 may be recirculated to the light ends column, preferably to a point below where sidedraw 128 was removed from light ends column, in order to improve the separation (not shown).

Since sidedraw 128 contains water in addition to acetic acid, sidedraw 128 from the light ends column 124 preferably is directed to drying column 130, in which the acetic acid and water are separated from one another. As shown, drying column 130, separates acetic acid sidedraw 128 to form overhead stream 144 comprised primarily of water and a product stream 146 comprised primarily of acetic acid. Overhead stream 144 preferably is cooled and condensed in a phase separation unit, e.g., decanter 148, to form a light phase 150 and a heavy phase 122. As shown, a portion of the light phase is refluxed, as shown by stream 152 and the remainder of the light phase is returned to the reactor 104, as shown by stream 120. The heavy phase, which typically is an emulsion comprising water and methyl iodide, preferably is returned in its entirety to the reactor 104, as shown by stream 122, optionally after being combined with stream 120.

Exemplary compositions for the light phase of the drying column overhead are provided below in Table 3.

TABLE 3

Exemplary Light Phase Compositions from Drying Column Overhead

| | conc. (Wt. %) | conc. (Wt. %) | conc. (Wt. %) |
|---|---|---|---|
| HOAc | 1-20 | 1-15 | 1-10 |
| Water | 50-90 | 60-90 | 70-90 |
| MeI | <10 | <5 | <3 |
| MeAc | 1-20 | 1-15 | 1-10 |

In certain embodiments, as discussed, minor amounts of an alkali component such as KOH can be added to sidedraw 128 via line 160 prior to entering the drying column 130. In other embodiments, the alkali component might also be added to the drying column 130 at the same height level as the stream 128 entering the drying column 130 or at a height above the height level height level as the stream 128 entering the drying column 130. Such addition can neutralize HI in the column.

Product stream 146 preferably comprises or consists essentially of acetic acid. In further embodiments, it is preferred not to dilute product stream 146 with an aqueous diluent, such as water. In one embodiment, product stream 146 comprises acetic acid at a concentration of greater than or equal to 99.5 wt. %, e.g., greater than or equal to 99.7 wt. % or greater than or equal to 99.9 wt. %. Product stream 146 comprises water at a concentration of no more than 0.2 wt. %, e.g., no more than 0.15 wt. %, no more than 0.1 wt. %, or no more than 0.05 wt. %. Due to anhydrous conditions in drying column 130, acetic anhydride may be formed. In one embodiment, product stream 146 comprises acetic anhydride at a concentration of no more than 600 wppm, e.g., no more than 500 wppm, no more than 450 wppm, no more than 400 wppm, no more than 300 wppm, no more than 200 wppm, no more than 100 wppm, or no more than 50 wppm. In terms of ranges, product stream 146 comprises acetic anhydride in an amount from 5 to 600 wppm, e.g., from 5 to 500 wppm, from 5 to 450 wppm, from 10 to 450 wppm, from 10 to 300 wppm, or from 10 to 100 wppm.

In some embodiments, in addition to acetic anhydride, product stream 146 may also comprise lithium in an amount of up to or equal to 10 wppm, e.g., up to or equal to 5 wppm, up to or equal to 1 wppm, up to or equal to 500 wppb, up to or equal to 300 wppb, or up to or equal to 100 wppb.

Thus, in one embodiment, there is provided a process for producing acetic acid comprising separating a reaction medium formed in a reactor in a flash vessel to form a liquid recycle and a vapor product stream, distilling the vapor product stream in a first column to obtain a side stream and a low boiling overhead vapor stream comprising water in an amount of greater than or equal to 5 wt. %, condensing the low boiling overhead vapor stream and biphasically separating the condensed stream to form a heavy liquid phase and a light liquid phase, optionally treating a portion of the heavy liquid phase and/or the light liquid phase to remove at least one PRC, distilling the side stream in a second column to obtain a product stream comprising acetic acid, water at a concentration of no more than 0.2 wt. % and acetic anhydride at a concentration of no more than 600 wppm, and contacting the product stream with a cation exchange resin to form a purified acetic acid product comprising no more than 50 wppm acetic anhydride.

Figure 2:
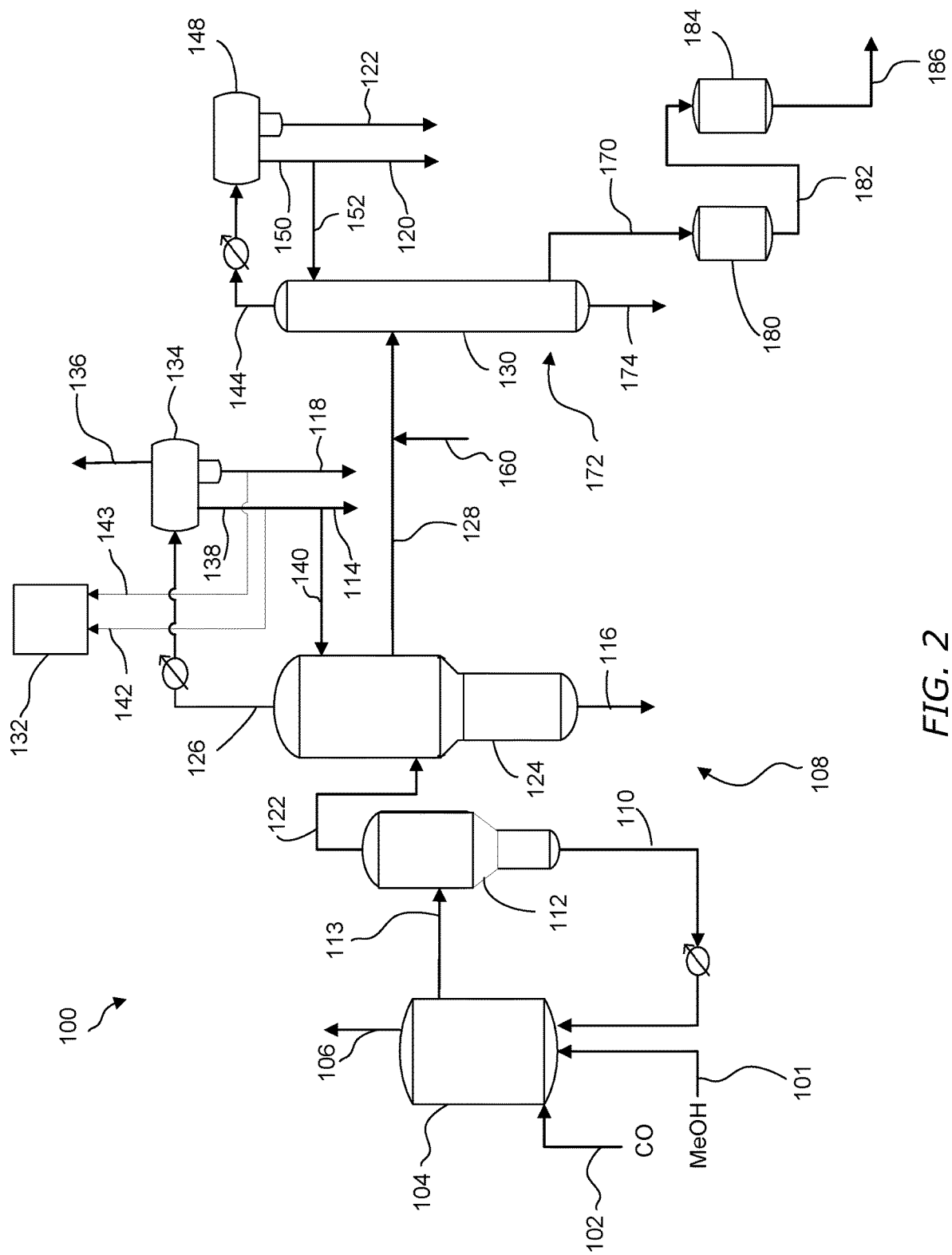
FIG. 2 illustrates another process for purifying acetic acid from a sidedraw with cation exchange resin to hydrate acetic anhydride and a metal functionalized fixed resin bed for iodide removal.

As shown in FIG. 2, in certain embodiments, the product stream withdrawn from the drying column 130 may be taken from a sidedraw 170 at a position slightly above the bottom 172 of the column 130. In one embodiment, sidedraw 170 is withdrawn within 5 actual stages from the bottom 172 of the column 130, e.g., within 4 actual stages from the bottom of the column 130, within 3 actual stages from the bottom of the column 130, or within 2 actual stages from the bottom of the column 130. In some embodiments, the sidedraw 170 is withdrawn a position between 2 and 5 actual stages from the bottom 172 of the column 130, e.g., a position between 3 and 5 trays from the bottom of the column 130, or position between 3 and 4 trays from the bottom of the column 130. In one embodiment, the product stream may be in sidedraw 170 that is withdrawn in the liquid phase so that the lithium cation concentration would be similar to the withdrawn lithium cation concentration in the drying columns bottoms in stream 146. In other embodiments, sidedraw 170 may be a vapor stream and the lithium cation concentration may be less than the bottoms stream 146. When in the vapor phase, it is desirable to condense sidedraw 170 prior to contacting the cationic exchanger resin. When a sidedraw 170 is used then other impurities such as heavy carbonyl containing groups, i.e. propionic acid, may advantageously concentrate in the bottoms stream 174. Residue stream 174 may be discarded or purged from the process 100.

Sidedraw 170 contains the product stream that is contacted with the cationic exchange resin to hydrate acetic anhydride according to embodiments of the present invention. In one embodiment there is provided a process for producing acetic acid comprising separating a reaction medium formed in a reactor in a flash vessel to form a liquid recycle and a vapor product stream, distilling the vapor product stream in a first column to obtain a side stream and a low boiling overhead vapor stream comprising water in an amount of greater than or equal to 5 wt. %, condensing the low boiling overhead vapor stream and biphasically separating the condensed stream to form a heavy liquid phase and a light liquid phase, optionally treating a portion of the heavy liquid phase and/or the light liquid phase to remove at least one PRC, distilling the side stream in a second column to obtain a sidedraw, either in the liquid or vapor phase, wherein the sidedraw comprises acetic acid, water at a concentration of no more than 0.2 wt. % and acetic anhydride at a concentration of no more than 600 wppm, and contacting the sidedraw, or a condensed portion thereof, with a cation exchange resin to form a purified acetic acid product comprising no more than 50 wppm acetic anhydride.

In some embodiments, the product stream withdrawn from the bottoms or the sidedraw may also be processed to remove lithium derived from and/or generated by the lithium compound in the reaction medium, by passing through cationic exchanger in the acid form and then through metal functionalized iodide removal ion exchange resins, prior to being stored or transported for commercial use. As described herein, cationic exchanger in the acid form are suitable for removing cations, such as lithium derived from and/or generated by compounds in the reaction medium that concentrate in the crude acid product. Once these components, and in particular lithium, are removed the iodides may be removed by metal functionalized iodide removal ion exchange resins.

Iodide Removal Beds/Use of Ion Exchange Resins

According to the present process, product stream that are contaminated with acetic anhydride and halides (e.g., iodides) may be contacted with an acid-form cationic exchange resin to hydrate the acetic anhydride followed by a metal-exchanged ion exchange resin having acid cation exchange sites comprising at least one metal selected from the group consisting of silver, mercury, palladium and rhodium under a range of operating conditions. Preferably, the ion exchange resin compositions are provided in fixed beds. The use of fixed iodide removal beds to purify contaminated carboxylic acid streams is well documented in the art (see, for example, U.S. Pat. Nos. 4,615,806; 5,653, 853; 5,731,252; and 6,225,498, which are hereby incorporated by reference in their entireties). Generally, a contaminated liquid carboxylic acid stream is contacted with the aforementioned ion exchange resin compositions, by flowing through a series of static fixed beds. In one embodiment, the cationic exchange resin may be used to hydrate at least 60% of the acetic anhydride in the product stream to yield a purified acetic acid product having acetic anhydride at a concentration of no more than 50 wppm. In some embodiments, cations, such as lithium contaminants may also be removed by the cationic exchange resin in the acid form. The halide contaminants, e.g., iodide contaminants, are then removed by reaction with the metal of the metal-exchanged ion exchange resin to form metal iodides. In some embodiments, hydrocarbon moieties, e.g., methyl groups, that may be associated with the iodide may esterify the carboxylic acid. For example, in the case of acetic acid contaminated with methyl iodide, methyl acetate would be produced as a byproduct of the iodide removal. The formation of this esterification product typically does not have a deleterious effect on the treated carboxylic acid stream.

Similar iodide contamination issues may exist in acetic anhydride manufactured via a rhodium-iodide catalyst system. Thus, the inventive process may alternatively be utilized in the purification of crude acetic anhydride product streams.

Suitably stable ion exchange resins utilized in connection with the present invention for preparing silver or mercury-exchanged resins for iodide removal typically are of the "RSO$_3$H" type classified as "strong acid," that is, sulfonic acid, cation exchange resins of the macroreticular (macroporous) type. Particularly suitable ion exchange substrates include Amberlyst® 15, Amberlyst® 35 and Amberlyst® 36 resins (DOW) suitable for use at elevated temperatures. Other stable ion exchange substrates such as zeolites may be employed, provided that the material is stable in the organic medium at the conditions of interest, that is, will not chemically decompose or release silver or mercury into the organic medium in unacceptable amounts. Zeolite cationic exchange substrates are disclosed, for example, in U.S. Pat. No. 5,962,735, the disclosure of which is incorporated herein by reference.

At temperatures greater than about 50° C., the silver or mercury exchanged cationic substrate may tend to release small amounts of silver or mercury on the order of 500 wppb or less and thus the silver or mercury exchanged substrate is chemically stable under the conditions of interest. More preferably, silver losses are less than 100 wppb into the organic medium and still more preferably less than 20 wppb into the organic medium. Silver losses may be slightly higher upon start up. In any event, if so desired a bed of acid form cationic material may be placed downstream of the silver or mercury exchange material in addition to the bed of acid form cationic material upstream of the silver or mercury exchange material, to catch any silver or mercury released.

The pressures during the contacting steps with the exchange resins are limited only by the physical strength of the resins. In one embodiment, the contacting is conducted at pressures ranging from 0.1 MPa to 1 MPa, e.g., from 0.1 MPa to 0.8 MPa or from 0.1 MPa to 0.5 MPa. For convenience, however, both pressure and temperature preferably may be established so that the contaminated carboxylic acid stream is processed as a liquid. Thus, for example, when operating at atmospheric pressure, which is generally preferred based on economic considerations, the temperature may range from 17° C. (the freezing point of acetic acid) to 118° C. (the boiling point of acetic acid). It is within the purview of those skilled in the art to determine analogous ranges for product streams comprising other carboxylic acid compounds. The temperature of the contacting step preferably is kept low enough to minimize resin degradation. In one embodiment, the contacting is conducted at a temperature ranging from 25° C. to 120° C., e.g., from 25° C. to 100° C. or from 50° C. to 100° C. Some cationic macroreticular resins typically begin significant degrading (via the mechanism of acid-catalyzed aromatic desulfonation) at temperatures of 150° C. Carboxylic acids having up to 5 carbon atoms, e.g., up to 4 carbon atoms, or up to 3 carbon atoms, remain liquid at these temperatures. Thus, the temperature during the contacting should be maintained below the degradation temperature of the resin utilized. In some embodiments, the operating temperature is kept below temperature limit of the resin, consistent with liquid phase operation and the desired kinetics for lithium and/or halide removal.

The configuration of the resin beds within an acetic acid purification train may vary, but the cationic exchanger should be upstream of the metal-exchanged resin. In a preferred embodiment, the resin beds are configured after a drying column. Preferably the resin beds are configured in a position wherein the temperature of the product stream is low, e.g., less than 120° C. or less than 100° C. The stream contacting the acid-form cationic exchange resin and the stream contacting the metal-exchanged resin can be adjusted to the same or different temperatures. For example, the stream contacting the acid-form cationic exchange resin can be adjusted to a temperature from 25° C. to 120° C., e.g., 30°

C. to 100° C., 25° C. to 85° C., 40° C. to 70° C., e.g., 40° C. to 60° C., while the stream contacting the metal-exchanged resin can be adjusted to a temperature from 50° C. to 100° C., e.g., from 50° C. to 85° C., from 55° C. to 75° C., or from 60° C. to 70° C. Aside from the advantages discussed above, lower temperature operation provides for less corrosion as compared to higher temperature operation. Lower temperature operation provides for less formation of corrosion metal contaminants, which, as discussed above, may decrease overall resin life. Also, because lower operating temperatures result in less corrosion, vessels advantageously need not be made from expensive corrosion-resistant metals, and lower grade metals, e.g., standard stainless steel, may be used.

Referring back to FIG. 1, product stream 146 is first passed through cationic exchange resin bed 180 to hydrate acetic anhydride. Although one cationic exchange resin bed 180 is shown, it should be understood that a plurality of cationic exchange resin beds may be used in series or parallel. In some embodiments, the cationic exchangers may also remove other cations present in the stream, such as lithium or potassium, if added via line 160 to drying column 130 as a potassium salt selected from the group consisting of potassium acetate, potassium carbonate, and potassium hydroxide, and corrosion metals. Using the cationic exchangers of the present invention, the purified acetic acid product comprises less acetic anhydride than the product stream.

The resulting purified acetic acid 182 may passes through a metal-exchanged ion exchange resin bed 184 having acid cation exchange sites comprising at least one metal selected from the group consisting of silver, mercury, palladium and rhodium to remove iodides from the stream to produce a purified product 186. Although one metal-exchanged ion exchange resin bed 184 is shown, it should be understood that a plurality of metal-exchanged ion exchange resin beds may be used in series or parallel. In addition to the resin beds, heat exchangers (not shown) may be located before either resin bed to adjust the temperature of the stream 146 and 182 to the appropriate temperature before contacting the resin beds. Similarly in FIG. 2, the crude acetic acid product is fed to cationic exchange resin bed 180 from side stream 170. Heat exchangers or condensers may be located before either resin bed to adjust the temperature of the stream 170 to the appropriate temperature before contacting the resin beds.

In one embodiment, the flow rate through the resin beds ranges from 0.1 bed volumes per hour ("BV/hr") to 50 BV/hr, e.g., 1 BV/hr to 20 BV/hr or from 6 BV/hr to 10 BV/hr. A bed volume of organic medium is a volume of the medium equal to the volume occupied by the resin bed. A flow rate of 1 BV/hr means that a quantity of organic liquid equal to the volume occupied by the resin bed passes through the resin bed in a one hour time period.

A purified acetic acid composition is obtained as a result of the resin bed treatment. The purified acetic acid composition comprises acetic anhydride at a concentration of no more than 50 wppm, e.g., no more than 40 wppm, no more than 30 wppm, no more than 20 wppm, no more than 10 wppm or no more than 5 wppm. In terms of ranges, the purified acetic acid product comprises acetic anhydride at a concentration from 0.5 to 50 wppm, e.g., from 0.5 to 40 wppm, from 0.5 to 30 wppm, from 0.5 to 20 wppm, or from 0.5 to 10 wppm. The purified acetic acid product comprises less acetic anhydride than the product stream. The purified acetic acid composition, in one embodiment, comprises iodides in an amount of no more than 100 wppb, e.g., no more than 90 wppb, no more than 50 wppb, no more than 25 wppb, or no more than 15 wppb. In one embodiment, the purified acetic acid composition comprises lithium in an amount of no more than 100 wppb, e.g., no more than 50 wppb, no more than 20 wppb, or no more than 10 wppb. In terms of ranges, the purified acetic acid composition may comprise from 0 to 100 wppb iodides, e.g., from 0 to 50 wppb, from 1 to 50 wppb, from 2 to 40 wppb; and/or from 0 to 100 wppb lithium, e.g., from 1 to 50 wppb, from 2 to 40 wppb. In other embodiments, the resin beds remove at least 25 wt. % of the iodides from the product stream, e.g., at least 50 wt. % or at least 75 wt. %.

In addition to reducing acetic anhydride, the present invention may also reduce a metal displaced from the metal-exchanged ion exchange resin, e.g. silver, mercury, palladium and rhodium, that undesirably accumulate in the purified acetic acid as the final product when no cationic exchanger is used to remove cations, such as lithium derived from and/or generated by the lithium compound in the reaction medium. In one embodiment, the purified acetic acid comprises a metal displaced from the metal-exchanged ion exchange resin, e.g., silver, mercury, palladium and rhodium, in an amount of no more than 100 wppb, e.g., no more than 90 wppb, no more than 80 wppb, no more than 70 wppb, no more than 60 wppb, no more than 50 wppb, no more than 40 wppb, no more than 30 wppb, or no more than 20 wppb. In terms of ranges, the purified acetic acid comprises a metal displaced from the metal-exchanged ion exchange resin, e.g., silver, mercury, palladium and rhodium, in an amount from 0 to 100 wppb, e.g., from 0.1 to 100 wppb, from 0.5 to 90 wppb, from 1 to 80 wppb, from 1 to 70 wppb, from 1 to 60 wppb, from 1 to 50 wppb, from 1 to 40 wppb, from 1 to 30 wppb, or from 1 to 20 wppb.

Distillation

The distillation columns of the present invention may be a conventional distillation column, e.g., a plate column, a packed column, and others. Plate columns may include a perforated plate column, bubble-cap column, Kittel tray column, uniflux tray, or a ripple tray column. For a plate column, the theoretical number of plates is not particularly limited and depending on the species of the component to be separate, may include up to 80 plates, e.g., from 2 to 80, from 5 to 60, from 5 to 50, or more preferably from 7 to 35. The distillation column may include a combination of different distillation apparatuses. For example, a combination of bubble-cap column and perforated plate column may be used as well as a combination of perforated plate column and a packed column.

The distillation temperature and pressure in the distillation system can suitably be selected depending on the condition such as the species of the objective carboxylic acid and the species of the distillation column, or the removal target selected from the lower boiling point impurity and the higher boiling point impurity according to the composition of the feed stream. For example, in a case where the purification of acetic acid is carried out by the distillation column, the inner pressure of the distillation column (usually, the pressure of the column top) may be from 0.01 to 1 MPa, e.g., from 0.02 to 0.7 MPa, and more preferably from 0.05 to 0.5 MPa in terms of gauge pressure. Moreover, the distillation temperature for the distillation column, namely the inner temperature of the column at the temperature of the column top, can be controlled by adjusting the inner pressure of the column, and, for example, may be from 20 to 200° C., e.g., from 50 to 180° C., and more preferably from 100 to 160° C.

The material of each member or unit associated with the distillation system, including the columns, valves, condensers, receivers, pumps, reboilers, and internals, and various lines, each communicating to the distillation system may be made of suitable materials such as glass, metal, ceramic, or combinations thereof, and is not particularly limited to a specific one. According to the present invention, the material of the foregoing distillation system and various lines are a transition metal or a transition-metal-based alloy such as iron alloy, e.g., a stainless steel, nickel or nickel alloy, zirconium or zirconium alloy thereof, titanium or titanium alloy thereof, or aluminum alloy. Suitable iron-based alloys include those containing iron as a main component, e.g., a stainless steel that also comprises chromium, nickel, molybdenum and others. Suitable nickel-based alloys include those alloys containing nickel as a main component and one or more of chromium, iron, cobalt, molybdenum, tungsten, manganese, and others, e.g., HASTELLOY™ and INCONEL™. Corrosion-resistant metals may be particularly suitable as materials for the distillation system and various lines.

As is evident from the figures and text presented above, a variety of embodiments are contemplated.

The present invention will be better understood in view of the following non-limiting examples.

EXAMPLES

Example 1

A stream comprising acetic acid, less than 2 wt. % water, and acetic anhydride that varied from 123 to 510 ppm was fed to a column filled with Ag functionalized sulfonic resin at 8 bed volume per hour flow rate. The temperature of the resin was controlled at 75° C. The acetic anhydride concentration in the inlet and outlet of the resin column were measured by a gas chromatograph (GC) equipped with a flame ionization detector. A capillary column with dimethylpolysiloxane stationary phase was used to achieve separation in the GC analysis. Results for experiments 1-3 are shown in Table 4.

TABLE 4

Flow Through Experiments Performed at 75° C.

| Experiment No. | Inlet Conc., ppm | Outlet Conc., ppm |
| --- | --- | --- |
| 1 | 123 | 2 |
| 2 | 235 | 2 |
| 3 | 510 | 1 |

Example 2

Experiments 4-6 were performed with the same procedures and setup as Example 1 except the initial acetic anhydride concentration varied from 171 to 574 ppm and the resin column temperature that was controlled at 25° C. Results are shown in Table 5.

TABLE 5

Flow Through Experiments Performed at 25° C.

| Experiment No. | Inlet Conc., ppm | Outlet Conc., ppm |
| --- | --- | --- |
| 4 | 171 | 1 |
| 5 | 333 | 1 |
| 6 | 574 | 2 |

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited below and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A process for producing acetic acid comprising:
   carbonylating, in a reactor, at least one member selected from the group consisting of methanol, dimethyl ether, and methyl acetate in a reaction medium comprising water, a rhodium catalyst, methyl iodide, and an iodide salt;
   separating the reaction medium to form a liquid recycle stream and a vapor product stream;
   distilling at least a portion of the vapor product stream in a first column to obtain an overhead and a side stream and withdrawing the side stream;
   i. biphasically separating the overhead to form a light phase comprising water and a heavy phase comprising methyl iodide and at least one permanganate reducing compound (PRC); and
   ii. treating at least a portion of the heavy phase to remove the at least one PRC;
   distilling the side stream in a second column to withdraw a product stream from a lower portion of the second column, the product stream comprising acetic acid and acetic anhydride, wherein the acetic anhydride is present at a concentration of no more than 600 wppm; and
   contacting the product stream with a metal ion-exchanged resin to reduce acetic anhydride concentrations and to yield a purified acetic acid product containing silver at a concentration of less than 100 wppb and acetic anhydride at a concentration of no more than 50 wppm.

2. The process of claim 1, wherein the purified acetic acid product has an acetic anhydride at a concentration of no more than 10 wppm acetic anhydride.

3. The process of claim 1, wherein the acetic anhydride concentration in the purified acetic acid product is less than the acetic anhydride concentration in the product stream.

4. The process of claim 1, wherein the metal ion-exchanged resin comprises at least 1% of strong acid exchange sites occupied by one or more of silver, mercury, palladium, and rhodium.

5. The process of claim 1, wherein the product stream is contacted with the metal ion-exchanged resin in a vessel being made of iron alloy, nickel or nickel alloy, zirconium or zirconium alloy thereof, titanium or titanium alloy thereof, or aluminum alloy.

6. The process of claim 5, wherein the vessel is operated at a temperature of less than 120° C. and a pressure ranging from 0.1 MPa to 1 MPa.

7. The process of claim 1, wherein the product stream has an iodide concentration from 20 wppb to 1.5 wppm.

8. The process of claim 7, wherein the purified acetic acid product has concentration of iodides being less than 100 wppb, provided that the concentration of iodides in the purified acetic acid product is less than the product stream.

9. The process of claim 1, wherein the product stream is removed through a sidedraw from the second column.

10. The process of claim 1, wherein the product stream is withdrawn at a point within 5 actual stages from the base of the second column.

11. The process of claim 1, wherein the product stream contains acetic acid at a concentration of greater than or equal to 99.5 wt. %.

12. The process of claim 1, wherein an alkali component is added to the side stream prior to step d).

13. The process of claim 1, wherein the heavy phase is treated to remove the at least one PRC using at least a distillation column.

14. The process of claim 1, further comprising returning a remaining portion of the heavy phase not treated to the reactor.

15. The process of claim 1, wherein the heavy phase has a methyl iodide concentration from 40 wt. % to 98 wt. %.

16. The process of claim 1, wherein a portion of the light phase is refluxed to the first column.

17. The process of claim 1, wherein the acetic anhydride concentration of the product stream is reduced by a hydration reaction.

18. The process of claim 1, wherein the at least PRC comprises acetaldehyde.

19. The process of claim 1, wherein the side stream comprises one or more $C_1$-$C_{14}$ alkyl iodides in an amount from 0.1 to 6 wt. % and hydrogen iodide at a concentration of no more than 300 wppm.

20. The process of claim 1, wherein the distilling of the side stream in the second column further yields an overhead having a methyl iodide concentration of less than or equal to 10 wt. %.

* * * * *